United States Patent [19]

Goto et al.

[11] Patent Number: 5,116,861

[45] Date of Patent: May 26, 1992

[54] NITROSOTHIOL DERIVATIVES AND THEIR USE

[75] Inventors: Giichi Goto, Toyono; Shigenori Ohkawa, Takatsuki; Shoji Fukumoto, Kobe, all of Japan

[73] Assignee: Takeda Chemical Industries, Ltd., Osaka, Japan

[21] Appl. No.: 562,626

[22] Filed: Aug. 3, 1990

[30] Foreign Application Priority Data

Aug. 7, 1989 [JP] Japan .................. 1-204361
Jan. 25, 1990 [JP] Japan .................. 2-015240

[51] Int. Cl.$^5$ .................. A61K 31/40; A61K 31/195; C07D 207/09; C07C 323/07
[52] U.S. Cl. .................. 514/427; 514/238.2; 514/255; 514/357; 514/358; 514/419; 514/538; 514/550; 514/562; 514/593; 544/160; 544/400; 546/331; 548/535; 558/414; 558/436
[58] Field of Search .................. 562/426; 560/9; 564/183, 154, 184, 162, 185, 199, 200, 48, 59, 340; 514/419, 238.2, 427, 255, 538, 357, 550, 358, 562, 593; 544/160, 400; 546/331; 548/535; 558/414, 436

[56] References Cited

U.S. PATENT DOCUMENTS 4,745,124 5/1988 Ryan et al. .................. 514/362

OTHER PUBLICATIONS

Ignarro et al., *The Journal of Pharmacology and Experimental Therapeutics*, vol. 218, (1981), pp. 739-749.

Primary Examiner—Michael L. Shippen
Assistant Examiner—Vera C. Clarke
Attorney, Agent, or Firm—Wegner, Cantor, Mueller & Player

[57] ABSTRACT

Novel nitrosothiol derivatives of the formula:

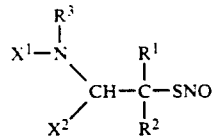

wherein $R^1$ and $R^2$ are independently a hydrogen atom or a hydrocarbon residue which may be substituted; $R^3$ is a hydrogen atom, an acyl group or a hydrocarbon residue which may be substituted; $X^1$ is a hydrogen atom, an acyl group, a lower alkoxy group or a hydrocarbon residue which may be substituted; $X^2$ is an acyl group or a carboxyl group which may be esterified or which may form an amide; with proviso that when $X^2$ is a carboxyl group $X^1$ is not a hydrogen atom or acetyl group and that when both $R^1$ and $R^2$ are hydrogen atoms $X^1$ is not acetyl group or γ-glutamyl group, and salts thereof, show excellent hypotensive action, antiarrhythmic action, anti-anginal action, cardiotonic action or coronary vasodilation, thus being useful as therapeutic or prophylactic agents for the cardiovascular diseases such as hypertension and angina pectoris.

33 Claims, No Drawings

NITROSOTHIOL DERIVATIVES AND THEIR USE

BACKGROUND OF THE INVENTION

This invention relates to novel S-nitrosothiol derivatives which are useful as medicines, especially as therapeutics for cardiovascular diseases such as hypertension and angina pectoris.

Along with aging of the society, hypertension and heart diseases have become matters of primary concern, and various cardiovascular medicines have been developed for the treatment of such diseases. There is prior art regarding the production of some nitro-compounds and nitrites among the medicines [Journal of Pharmacy and Pharmacology, 31, 801 (1979)].

In the social circumstances described above, more reasonable agents are being required to be developed in the field of cardiovascular drugs, particularly antihypertensives and therapeutics for angina pectoris. However, satisfactory compounds have not yet been found. There have been no reports so far as to the application of S-nitrosothiol derivatives as therapeutics for angina pectoris.

DETAILED DESCRIPTION

As the result of the research to find useful compounds as therapeutics for cardiovascular diseases, especially as anti-hypertensives and therapeutics for angina pectoris, the present inventors have found that the compounds represented by the formula (1):

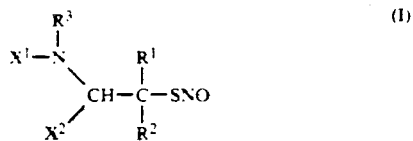

wherein $R^1$ and $R^2$ represent respectively a hydrogen atom or a hydrocarbon residue which may be substituted; $R^3$ is a hydrogen atom, an acyl group or a hydrocarbon residue which may be substituted; $X^1$ is a hydrogen atom, an acyl group, a lower alkoxy group or a hydrocarbon residue which may be substituted; $X^2$ is an acyl group or a carboxyl group which may be esterified or form an amide; and when $X^2$ is a carboxyl group $X^1$ is not a hydrogen atom or acetyl group, and when both $R^1$ and $R^2$ are hydrogen atoms $X^1$ is not acetyl group or gamma-glutamyl group, and the salts thereof are excellent in alleviation of the cardiovascular diseases, and have completed the present invention.

The "hydrocarbon residues" in the above-mentioned "hydrocarbon residues which may be substituted" in the formula (I) include, chain-, cyclic-, saturated-, and unsaturated-hydrocarbon residues, and various combinations thereof. Chain-hydrocarbon residues include straight chain and branched alkyl groups each having 1 to 6 carbon atoms (e.g. methyl, ethyl, n-propyl, i-propyl, n-butyl, i-butyl, tert-butyl, n-pentyl, n-hexyl).

Chain unsaturated hydrocarbon residues include straight chain and branched $C_{2-4}$-alkenyl (e.g. vinyl, allyl, 2-butenyl), and $C_{2-4}$-alkynyl (e.g. propargyl, 2-butynyl).

Cyclic saturated hydrocarbon residues include monocyclic cycloalkyl having 3 to 7 carbon atoms (e.g. cyclobutyl, cyclopentyl, cyclohexyl), and bridged cyclic saturated hydrocarbon residues having 8 to 14 carbon atoms (e.g. bicyclo[3,2,1]oct-2-yl, bicyclo[3,3,1]nonan-2-yl). Cyclic unsaturated hydrocarbon residues include phenyl and naphthyl groups.

$R^1$ and $R^2$ may be bound with each other to form a ring of $—(CH_2)_n—$ wherein n is an integer of 2 to 6.

Substituents for these hydrocarbon residues include halogen atoms (e.g. chlorine, bromine, and iodine atoms), nitro, nitrile, hydroxyl, carboxyl, $C_{1-4}$-alkoxy (e.g. methyloxy, ethyloxy, propyloxy, butyloxy, isopropyloxy), $C_{1-4}$-alkylthio (e.g. methylthio, ethylthio, propylthio, isopropylthio, butylthio), amino, mono- or di-$C_{1-4}$-alkyl substituted amino (e.g. methylamino, ethylamino, propylamino, dimethylamino, diethylamino), mono- or di-aralkyl substituted amino (e.g. benzylamino, 2-hydroxyphenylmethylamino), mono- or di-pyridylcarbonyl substituted amino (e.g. 3-pyridylcarbonylamino), $C_{1-4}$ alkoxycarbonyl (e.g. methoxycarbonyl, ethoxycarbonyl, propoxycarbonyl, isobutoxycarbonyl), hydroxycarbonyl, $C_{1-6}$-alkylcarbonyl (e.g. methylcarbonyl, ethylcarbonyl, butylcarbonyl), cyclo-$C_{3-6}$-alkylcarbonyl (e.g. cyclopentylcarbonyl, cyclohexylcarbonyl), carbamoyl, mono- or di-$C_{1-4}$-alkyl-substituted carbamoyl (e.g. methylcarbamoyl, ethylcarbamoyl, propylcarbamoyl, butylcarbamoyl, diethylcarbamoyl, dibutylcarbamoyl), and phenyl, phenoxy, benzoyl, phenoxycarbonyl, phenyl-$C_{1-4}$-alkylcarbamoyl (e.g. benzylcarbamoyl, phenethylcarbamoyl) and phenylcarbamoyl which may have 1 to 4 substituents [substituents in the respective phenyl group include $C_{1-4}$-alkyl group (e.g. methyl, ethyl, propyl, butyl, isopropyl), halogen atom (e.g. chlorine, bromine, iodine atoms), hydroxyl, benzyloxy, amino, mono- or di- $C_{1-4}$-alkyl-substituted amino (e.g. methylamino, ethylamino, propylamino, dimethylamino, diethylamino, methylethylamino), nitro, $C_{1-4}$-alkoxycarbonyl (e.g. methoxycarbonyl, ethoxycarbonyl, propoxycarbonyl)].

The appropriate number of the substitutents in each of these hydrocarbon residues is 1 to 3.

Acyl groups represented by $R^3$, $X^1$, and $X^2$ include carboxylic acyl, carbamic acyl, sulfonic acyl, and substituted oxycarboxylic acyl groups, all of which may be substituted. When an acyl group is substituted, the substituents include those for the hydrocarbon residues described above.

Carboxylic acyl groups include $C_{1-6}$alkylcarbonyl such as formyl, acetyl, propionyl, butyryl, valeryl, hexanoyl, isobutyryl, and isovaleryl (which may be substituted, for example, with amino, 3-carbamoyl-1,4-dihydropyridin-1-yl, 3-carbamoyl-1-pyridyl, or phenoxy; substituted $C_{1-6}$-alkylcarbonyl groups are exemplified by phenoxyacetyl, 4-aminobutyryl, aminomethylcarbonyl, 2-(3-carbamoyl-1,4-dihydropyridin-1-yl)ethylcarbamoyl, and 2-(3-carbamoylpyridin-1-yl)ethylcarbamoyl), $C_{3-8}$cycloalkylcarbonyl such as cyclopentylcarbonyl and cyclohexylcarbonyl, $C_{3-6}$cycloalkyl-$C_{1-6}$alkylcarbonyl such as cyclopentylacetyl, $C_{2-6}$alkenyl or alkynylcarbonyl such as acryloyl, crotonoyl, 2-pentenoyl, 4-pentynoyl, 2-hexenoyl, 3-hexenoyl, and 2,4-hexadienoyl, aryl carbonyl such as benzoyl, and naphthoyl, pyridylcarbonyl such as nicotinoyl, and dihydropyridylcarbonyl [which may be substituted, for example, with $C_{1-4}$alkyl (e.g. methyl, ethyl, propyl, butyl), benzyl, methoxycarbonyl, 3-nitrophenyl, nitro, or 2-trifluorophenyl; substituted dihydropyridylcarbonyl groups are exemplified by N-$C_{1-4}$alkyl-1,4-dihydropyridine-3-carbonyl (e.g. N-methyl-1,4-dihydropyridine-3-carbonyl, N-ethyl-1,4-dihydropyridine-3-carbonyl, N-butyl-1,4-dihydropyridine-3-carbonyl), N-benzyl-1,4- dihydropyridine-3carbonyl, 2,6-dimethyl-5-methoxycarbonyl-4-(3-nitrophenyl)-1,4-dihydropyridine-3-ylcarbonyl, and 2,6-dimethyl-5-nitro-4-(2-trifluorophenyl-1,4-dihydropyridine-3-ylcarbonyl)], pyridiniumcarbonyl (in which the nitrogen in the pyridine ring is substituted, for example with C₁₋₄alkyl (e.g. methyl, ethyl), or benzyl, and exemplified by C₁₋₄alkylpyridinium-3-carbonyl (e.g. methylpyridinium-3-carbonyl, ethylpyridinium-3-carbonyl, propylpyridinium-3-carbonyl, and benzylpyridinium-3-carbonyl).

Carbamic acyl groups include carbamoyl, mono- or di- substituted carbamoyl groups. The mono- and di-substituted carbamoyl groups include mono- and di-C₁₋₄ alkylcarbamoyl such as methylcarbamoyl, ethylcarbamoyl, propylcarbamoyl, butylcarbamoyl, dimethylcarbamoyl, diethylcarbamoyl, and dipropylcarbamoyl, mono- and di-C₃₋₆alkenyl- and alkynylcarbamoyl such as allylcarbamoyl, 3-butenylcarbamoyl, 4-pentenylcarbamoyl, and diallylcarbamoyl, mono- and di-aromatic group carbamoyl such as phenylcarbamoyl, naphthylcarbamoyl, and diphenylcarbamoyl.

Sulfonic acyl groups include inorganic sulfonyl such as sodiumsulfonyl, C₁₋₆alkylsulfonyl such as methylsulfonyl, ethylsulfonyl, propylsulfonyl, and butylsulfonyl, C₂₋₆alkenyl- or alkynylsulfonyl such as allylsulfonyl, and 2-methyl-2-propenesulfonyl, and aromatic sulfonyl such as phenylsulfonyl, p-methylphenylsulfonyl, and naphthalenesulfonyl.

Substituted oxycarboxylic acyl groups include C₁₋₆alkyloxycarbonyl which may be substituted with halogen (e.g. chlorine, bromine, iodine), cyano, benzyloxy, phenoxy, di-C₁₋₃alkylamino (e.g. dimethylamino, diethylamino, dipropylamino), C₁₋₄alkyloxy (e.g. methyloxy, ethyloxy, butyloxy, t-butyloxy), C₁₋₃alkylthio (e.g. methylthio, ethylthio, propylthio), 4-(3-nitrophenyl)-2,6-dimethyl-3-methoxycarbonyl-1,4-dihydropyridin-5-ylcarbonylamino or dihydropyridylcarbonylamino (methyloxycarbonyl, ethyloxycarbonyl, n-propyloxycarbonyl, i-propyloxycarbonyl, n-butyloxycarbonyl, secbutyloxycarbonyl, t-butyloxycarbonyl, n-hexyloxycarbonyl, 2-fluoroethyloxycarbonyl, 2-chloroethyloxycarbonyl, 2,2,2trichloroethyloxycarbonyl, and 3-methyl-1,4-dihydropyridin-1-ylcarbonylaminomethyloxycarbonyl), C₃₋₈cycloalkyloxycarbonyl (which may be substituted, for example, with halogen such as chlorine, bromine, and iodine) such as cyclopentyloxycarbonyl, and cyclohexyloxycarbonyl, C₃₋₈cycloalkyl-C₁₋₆alkyloxycarbonyl such as cyclopentylmethyloxycarbonyl, C₂₋₇alkenyl- or alkynyloxycarbonyl such as allyloxycarbonyl, crotyloxycarbonyl, and 2-pentene-1-oxycarbonyl, aromatic or aromatic-aliphatic oxycarbonyl (which may be substituted, for example, with halogen such as chlorine, bromine and iodine, or nitro) such as phenyloxycarbonyl, benzyloxycarbonyl, and phenethyloxycarbonyl, and quinuclidinyl.

Lower alkoxy groups represented by X¹ include those represented by the formula: —OR⁴ [wherein R⁴ represents an alkyl group having 1 to 6 carbo atoms (e.g. methyl, ethyl, propyl, i-propyl, butyl, t. ,t-butyl, hexyl)].

Esterified carboxyl groups represented by X² include those represented by the formula: —CO—OR⁵ [wherein R⁵ represents a hydrocarbon residue which may be substituted], and the "hydrocarbon residues which may be substituted" represented by R⁵ include the groups described above as "the hydrocarbon residues which may be substituted" represented by R¹, R², R³, or X¹.

Amide-forming carboxyl groups represented by X² include those represented by the formula:

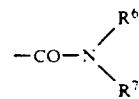

wherein R⁶ is a hydrogen atom or a hydrocarbon residue which may be substituted, and R⁷ is a hydrogen atom or a lower alkyl group. In the formula described above, the "hydrocarbon residues which may be substituted" represented by R⁶ include the "hydrocarbon residues which may be substituted" represented by R¹, R², R³, R⁵, or X¹, described above, and the lower alkyl groups represented by R⁷ include alkyl groups having 1 to 6 carbon atoms each (e.g. methyl, ethyl, n-propyl, i-propyl, n-butyl, i-butyl, tert-butyl, n-pentyl, n-hexyl). In the formula described above, R⁶ and R⁷ may constitute a cyclic amino group together with the adjacent nitrogen atom, and the cyclic amino groups formed by R⁶, R⁷, and the adjacent nitrogen atom include nitrogen-containing 5- to 7-membered heterocyclic groups, such as the groups represented by the formula:

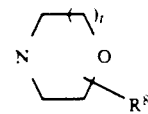

those represented by the formula:

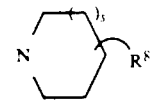

and those represented by the formula:

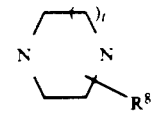

In these formula, s represents 0, 1, or 2, t represents 1, or 2, and R⁸ represents a substituent which the cyclic amino group formed by the R⁶, and R⁷ may have, or a hydrogen atom; the substituents include alkyl groups having 1 to 3 carbon atoms each (e.g. methyl, ethyl, propyl), oxo, hydroxy, phenyl, benzyl, and amino groups.

The groups represented by the formula:

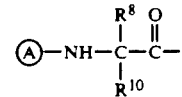

as X¹ when X¹ represents an acyl group, and the groups represented by the formula:

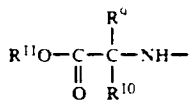

as the substituted amino groups when $X^2$ represents an amide-forming carboxyl group, represent the residues of amino acid derivatives, where the amino acids are not specified. The amino acids may be of D-form or L-form. $R^9$, $R^{10}$, and $R^{11}$ are the same or different, each representing a hydrogen atom or a lower alkyl group which may be substituted. $R^9$ and $R^{10}$ may bind to each other to form a lower alkylene chain represented by the formula: $-(CH_2)_m-$ (wherein m represents an integer of 2 to 4), and A represents a hydrogen atom, lower alkyl group, or acyl group.

The residues of amino acid derivatives described above include those of derivatives of amino acids such as glycine, alanine, glutamic acid, leucine, isoleucine, phenylalanine, aspartic acid, cysteine, sarcosine, glutamine, asparagine, and proline.

When the compound of the general formula (I) has an asymmetric carbon atom, the compound may be of D-, L- or DL-form, being unaffected by the asymmetry of the group represented by $X^1$ or $X^2$.

Among the compounds represented by the formula (I) described above, those excellent in chemical stability are desirable, and $R^1$ and $R^2$ may be any group that has a steric effect contributing to stabilization of a $-SNO$ group, being desirably a $C_{1-6}$alkyl group such as methyl, ethyl, or propyl, phenyl, or naphthyl; when $R^1$ and $R^2$ are bound to each other, the group formed by $R^1$ and $R^2$ together with the carbon atoms to which the groups are bound is desirably cyclopentyl or cyclohexyl.

$R^3$ is desirably a hydrogen atom, or a $C_{6-10}$ aromatic acyl group such as benzoyl, naphthoyl, or phenylacetyl. $X^1$ is desirably a hydrogen atom or an amino acid residue, and the amino acid is desirably glycine, aspartic acid, phenylalanine, asparagine, glutamic acid, or glutamine. $X^2$ is desirably carboxyl, carbonylamino, or carboxyl forming an amide with an amino acid residue, and the amino acid is desirably glycine, asparagine, glutamine, aspartic acid, glutamic acid, or phenylalanine.

Among the compounds represented by the formula (I) described above, are desirable those wherein each of $R^1$ and $R^2$ represents $C_{1-6}$alkyl group, phenyl, or naphthyl, or $R^1$ and $R^2$ form cyclopentyl or cyclohexyl together with the carbon atoms to which $R^1$ and $R^2$ are bound, $R^3$ is a hydrogen atom or a $C_{6-10}$ aromatic acyl group, $X^1$ is a hydrogen atom or an amino acid residue of which amino acid is selected from the group consisting of glycine, aspartic acid, phenylalanine, asparagine, glutamic acid, and glutamine, $X^2$ is a carboxyl group, carbonylamino or a carboxyl group forming an amide with an amino acid residue of which the amino acid is selected from the group consisting of glycine, aspartic acid, asparagine, glutamic acid, glutamine, and phenylalanine.

When the compound (I) of this invention is basic, the compound may form an acid adduct, especially a physiologically acceptable acid adduct; such adducts are exemplified by salts with inorganic acids (e.g. hydrochloric acid, nitric acid, phosphoric acid, hydrobromic acid), and salts with organic acids (e.g. acetic acid, propionic acid, fumaric acid, maleic acid, tartaric acid, citric acid, malic acid, oxalic acid, benzoic acid, methanesulfonic acid, benzenesulfonic acid).

The compounds of the general formula (I) can be produced by nitrosation of the compounds represented by the general formula (II).

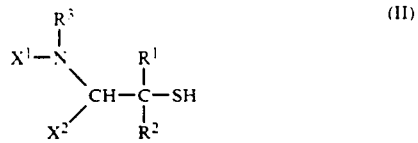

wherein $R^1$, $R^2$, $R^3$, $X^1$, and $X^2$ mean the same as above

Reagents generally used for the nitrosation of the compound (II) include nitrogen monoxide, nitrogen dioxide, dinitrogen tetraoxide, nitrosyl chloride, nitrous acid, and ethyl nitrite, but the reagents are not limited to these, and any reagent that can usually be used for nitrosation may be used.

The reaction may be conducted without any solvent or in a solvent. Any solvent may be used as far as it does not inhibit nitrosation, including water, alcohols (e.g. methanol, ethanol, propanol, butanol, tertbutanol), petroleum solvents (e.g. n-hexane, n-pentane, n-heptane), aromatic solvents (e.g. benzene, toluene, pyridine), ethers (e.g. ethyl ether, tetrahydrofuran, dioxane, isopropyl ether), amides (e.g. N,N-dimethylformamide, N,N-dimethylacetamide), esters (e.g. methyl acetate, ethyl acetate, butyl acetate), halogenated hydrocarbons (e.g. dichloromethane, chloroform, dichloroethane, carbon tetrachloride), and dimethyl sulfoxide.

The reaction can be conducted at $-30°$ C. to $150°$ C., but is desirably conducted at a lower temperature ($-5°$ C. to $30°$ C.). For one mole of the compound (II), desirably 1 to 5 moles of the nitrosating reagent are used. The reaction time varies depending on the properties of the compound (II) being generally 1 minute to 6 hours, desirably as short as 1 minute to 30 minutes.

The compounds (II) can be produced according to a per se known method [Angewandte Chemie, 87, 372 (1975)], for example, by the procedures shown as the Reaction Formulas 1 to 4.

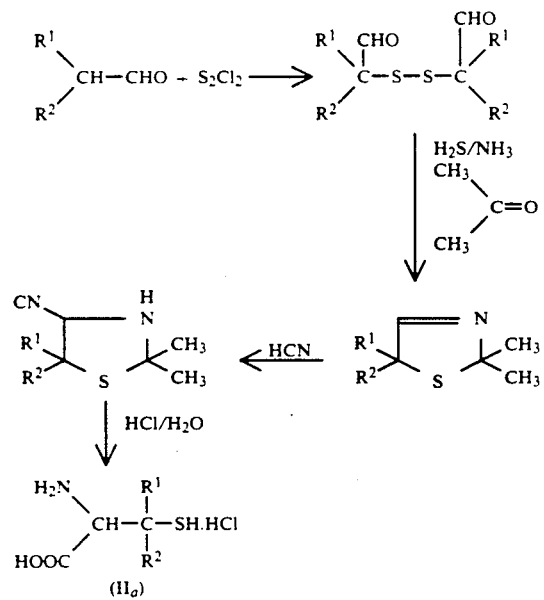

wherein the symbols are the same as described above.

Reaction Formula 1

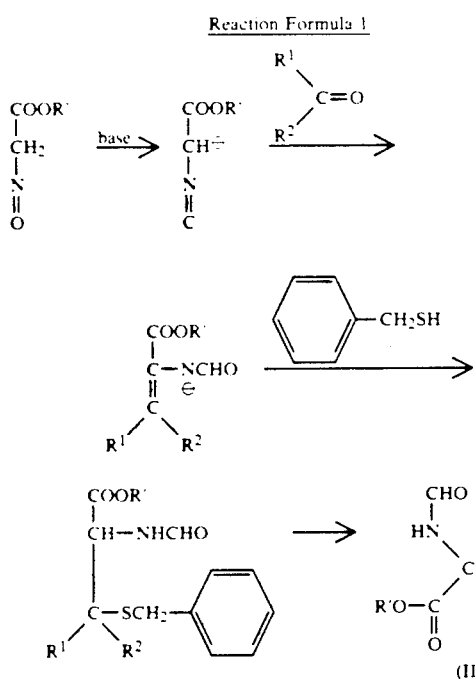

wherein R' is a $C_1$-lower alkyl or benzyl, and other symbols are the same as described above.

Reaction Formula 2

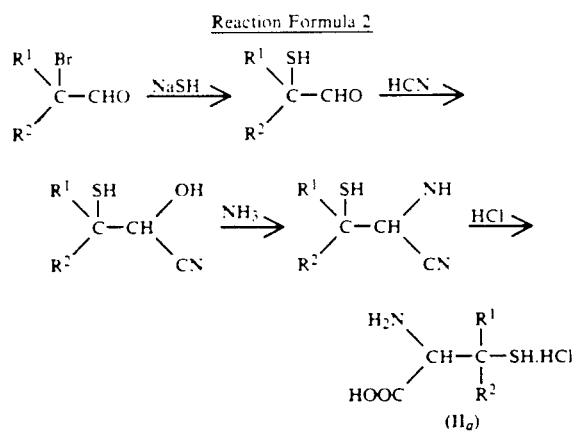

wherein the symbols are the same as described above.

Reaction Formula 3

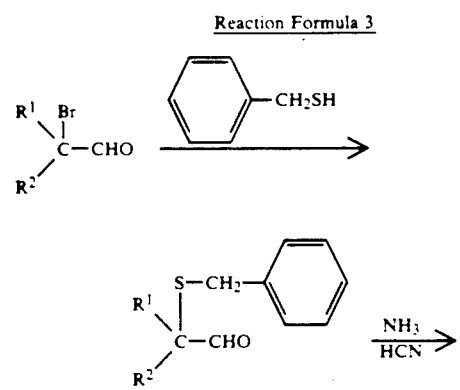

-continued
Reaction Formula 3

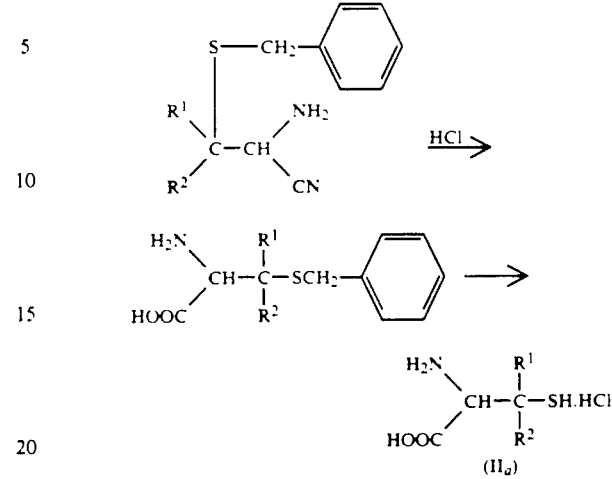

wherein the symbols are the same as described above.

Reaction Formula 4

The compound (IIa) or (IIb) thus obtained is further subjected to N-acylation, N-alkylation, N-peptide formation, or esterification, alkylation, or peptide formation at the C terminal, to give the compound (II).

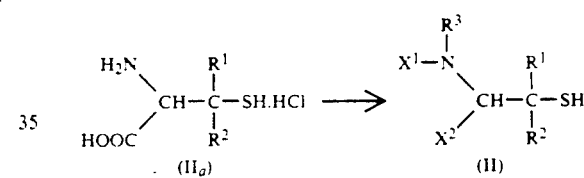

These reactions can be conducted according to a per se known method.

The compounds (I) of this invention act on the cardiovascular system of mammals, exerting excellent hypotensive action, anti-arrhythmic action, antianginal action, cardiotonic action, or coronary vasodilation.

The compounds (I) of this invention are excellent in duration and strength of the cardiovascular action as compared with the known nitro compounds such as nitroglycerine and nitrites, having no or only very mild undesirable side effects in the cardiovascular, psychic-nervous, or digestive system, such as dizziness, palpation, discomfort in the chest, arrhythmia, headache, fatigue, nausea, and vomiting. The compounds are remarkably effective after oral, parenteral, or percutaneous administration. Therefore the compounds are useful as therapeutics or prophylactics for various cardiovascular disorders in mammals including human. Among the compounds (I) of this invention, those that dilate selectively the coronary vessels are useful as prophylactics and therapeutics for angina pectoris.

The diseases for which the compounds (I) of this invention are useful include angina pectoris, myocardial infarction, cardiac asthma, achalasia (temporary remission), coronary sclerosis (chronic ischemic heart disease, asymptomatic ischemic heart disease, arteriosclerotic heart disease), maintaining hypotensive state during operation, emergency treatment of abnormal hypertension during operartion, acute heart failure, essential hypertension, and renal hypertension; the compounds can be used for prevention and treatment of these diseases.

The compounds of this invention as such or a stabilized conjugate thereof with cyclodextrin, etc. can be administered to mammals including human orally or parenterally in various forms such as tablets, granules, capsules, injections, suppositories, percutaneous preparations, buccal preparations (sublingual tablets), ointments, and cataplasms. The dose varies depending on the type of the disease to be treated and the symptom, the daily dose being generally 0.1 mg to 500 mg, desirably 1 mg to 30 mg for oral administration to an adult human.

In this specification, amino acids, protective groups, and others are sometimes shown by conventionally used abbreviations based on the IUPACIUB Commission on Biological Nomenclature. The abbreviations used are listed in the following.

Ac: acetyl
Boc: t-butoxycarbonyl
OBzl: benzylester
WSC: 1-ethyl-3-(3-dimethylaminopropyl)carbodiimide
HOBt: 1-hydroxybenzotriazole
Trt: trityl
Pen: penicillamine
Gly: glycine
Ala: alanine
Val: valine
Leu: leucine
Pro: proline
Phe: phenylalanine
Tyr: tyrosine
Glu: glutamic acid
Asp: aspartic acid The side chains of amino acid residues are represented as follows:

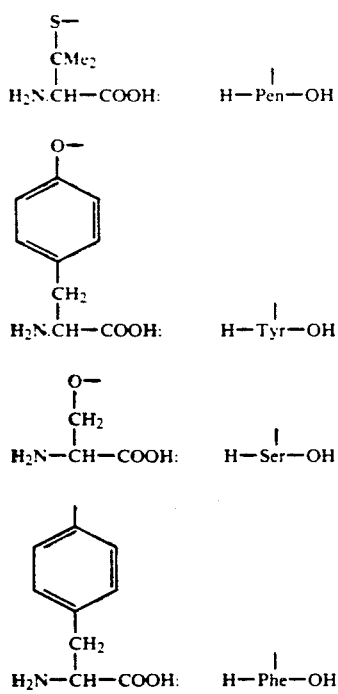

EXAMPLES

The following Reference Examples, Working Examples, Preparation Examples, and Experimental Examples explain this invention in more concrete, but should not limit this invention.

Reference Example 1 (Synthesis of the Compound A-1)

To the solution of S-trityl-L-penicillamine (69.5 g) and di-t-butyldicarbonate (46.5 g) in dichloromethane (1500 ml), was added triethylamine (20.2 ml) at 0° C., and the mixture was stirred at room temperature for 5 hours. To the reaction mixture were added ice and an aqueous solution of potassium hydrogensulfate. The organic layer was washed with an aqueous solution of potassium hydrogensulfate, water, and saturated saline, in this order, and dried over magnesium sulfate. The solvent was evaporated off under reduced pressure, to give N-t-butoxycarbonyl-S-trityl-L-penicillamine (87.0 g).

In the same way the Compound A-2 listed in Table 1 described below was synthesized.

Reference Example 2 (Synthesis of the Compound B-1)

To the solution of N-t-butoxycarbonyl-S-trityl-D-penicillamine (A-2) (6.0 g) in dimethylformamide (40 ml), were added methyl iodide (1.5 ml) and potassium hydrogencarbonate (2.4 g), and the mixture was stirred for 14 hours. To the reaction mixture was added ice-water, and the mixture was extracted with ethyl acetate. The organic layer was washed with water and then with saturated saline, and dried over magnesium sulfate. The solvent was evaporated off under reduced pressure, to give N-t-butoxycarbonyl-S-trityl-D-penicillamine methyl ester (6.0 g).

Reference Example 3 (Synthesis of the Compound B-2)

To the solution of N-t-butoxycarbonyl-S-trityl-L-penicillamine (A-1) (4.0 g) and 1-hydroxybenzotriazole (abbreviated as HOBt) (1.2 g) in chloroform (40 ml) and tetrahydrofuran (16 ml), was added dropwise by ice-cooling the solution of 1-ethyl-3-(3dimethylaminopropyl)carbodiimide (water-soluble carbodiimide: abbreviated as WSC) (1.7 g) in chloroform (10 ml). The mixture was stirred at the same temperature for 1 hour, then glycine ethyl ester hydrochloride (1.1 g) and triethylamine (0.85 ml) were added, and the mixture was stirred at room temperature for 12 hours. After addition of water, the organic layer was washed with an aqueous solution of potassium hydrogensulfate, water, an aqueous solution of sodium hydrogencarbonate, water and saturated saline, in this order, and dried over magnesium sulfate. The solvent was evaporated off under reduced pressure, and the residue was subjected to column chromatography, to give N-t-butoxycarbonyl-S-trityl-L-penicillamylglycine ethyl ester (4.5 g).

In the same way the Compounds B-3 to B-22 and D-30 listed in Table 1 described below were synthesized.

Reference Example 4 (Synthesis of the Compound C-2)

To the solution of N-t-butoxycarbonyl-S-trityl-L-penicillamylglycine ethyl ester (B-2) (4.5 g) and 2,6lutidine (2.8 ml) in dichloromethane (100 ml), was added dropwise at 0° C. the solution of trimethylsilyl trifluoromethanesulfonate (3.9 ml), and the mixture was stirred for 1 hour while the temperature was gradually returned to the room temperature. To the reaction mixture was added ice-water, and the organic layer was washed with 1N-hydrochloric acid, water, an aqueous solution of sodium hydrogencarbonate, water, and saturated saline, in this order, and dried over magnesium sulfate. The solvent was evaporated off under reduced pressure, to give S-trityl-L-penicillamylglycine ethyl ester (3.8 g)

In the same way the Compounds C-1, and C-3 to C-22 listed in Table 1 described below were synthesized.

Reference Example 5 (Synthesis of the Compound D-3)

To the solution of S-trityl-L-penicillamylglycine ethyl ester (C-2) (3.7 g) in dichloromethane (50 ml) were added acetyl chloride (0.66 ml) and triethylamine (0.88 ml) at 0° C. The mixture was stirred at the same temperature for 15 minutes and then ice water was added. The organic layer was washed with an aqueous potassium hydrogensulfate solution, water, an aqueous sodium hydrogencarbonate solution, water and saturated saline, in this order, and dried over magnesium sulfate. The solvent was evaporated off under reduced pressure, and the residue was subjected to silica gel column chromatography, to give N-acetyl-S-trityl-L-penicillamylglycine ethyl ester (3.5 g).

Reference Example 6 (Synthesis of the Compound D-4)

To the solution of S-trityl-L-penicillamylglycine ethyl ester (C-2) (5.4 g) and N-t-butoxycarbonyl-L-glutamic acid α-benzyl ester (3.8 g) in chloroform (100 ml) was added WSC (2.4 g) at 0° C., and the mixture was stirred at room temperature for 3 hours. To the reaction mixture was added ice water. The organic layer was washed with an aqueous potassium hydrogensulfate solution, water, aqueous sodium hydrogencarbonate solution, water and saturated saline, in this order, and dried over magnesium sulfate. The solvent was evaporated off under reduced pressure, and the residue was subjected to column chromatography, to give (4S)-4-t-butoxycarbonylamino-4-benzyloxycarbonylbutyryl-S-trityl-L-penicillamylglycine ethyl ester (8.4 g).

In the same way the Compounds D-1, D-2, D-5 to D-27 and D-29 listed in Table 1 described below were synthesized.

Reference Example 7 (Synthesis of the Compound E-5)

To the solution of (4S)-4-t-butoxycarbonylamino-4-benzyloxycarbonylbutyryl-S-trityl-L-penicillamylglycine ethyl ester (D-4) (8.4 g) in tetrahydrofuran (150 ml) was added 1N-sodium hydroxide (25.3 ml) and the mixture was stirred at room temperature for 2 hours. Tetrahydrofuran was evaporated off under reduced pressure, and the aqueous layer was washed twice with diethyl ether, then an aqueous potassium hydrogensulfate solution was added to make the aqueous layer acidic, and the solution was extracted with ethyl acetate. The organic layer was washed with water and saturated saline, and the solvent was evaporated off under reduced pressure, to give [N-γ-(N-t-butoxycarbonyl)-L-glutamyl-S-trityl-L-penicillamyl]glycine (7.0 g).

In the same way the Compounds E-1 to E-4, and E-6 to E-32 listed in Table 1 described below were synthesized.

Reference Example 8 (Synthesis of the Compound F-5)

The solution of [N-γ-(N-t-butoxycarbonyl)-L-glutamyl-S-trityl-L-penicillamyl]glycine (E-5) (3.0 g) in chloroform (60 ml) was bubbled with hydrogen chloride gas at 0° C. for 30 minutes. To the reaction mixture was added diethyl ether, and the crystals were collected by filtration and washed with diethyl ether. The crystals were dried under reduced pressure, to give (N-γ-L-glutamyl-L-penicillamyl)glycine hydrochloride (1.7 g).

In the same way the Compounds F-1 to F-4, and F-6 to F-32 listed in Table 1 described below were synthesized.

Reference Example 9 (Synthesis of the Compound B-23)

To the solution of N-t-butoxycarbonyl-S-trityl-L-penicillamine (A-1)(4.0 g) and HOBt (1.2 g) in chloroform (40 ml) and tetrahydrofuran (15mg), was added dropwise under ice-cooling the solution of WSC (1.7 g) in chloroform (10mg). The mixture was stirred at the same temperature for 1 hour, water was added, and the organic layer was washed with an aqueous solution of potassium hydrogensulfate, water, an aqueous solution of sodium hydrogencarbonate, water and saturated saline, in this order, and dried over magnesium sulfate. The solvent was evaporated off under reduced pressure, to give HOBt ester.

To the solution of p-sulfophenylalanine (2.0 g) in water (40 ml), sodium hydrogencarbonate (1.2 g) was added. To this solution, the solution of the HOBt ester synthesized as described above in dioxane (40 ml) was added, followed by addition of tetrabutylammonium hydrogensulfate (3.3 g), and the mixture was stirred at room temperature for 1 hour. The solvent was evaporated off under reduced pressure and the residue was extracted with chloroform. The organic layer was washed with an aqueous solution of potassium hydrogensulfate, water and saturated saline, in this order, and dried over magnesium sulfate. The solvent was evaporated off under reduced pressure, to give tetrabutylammonium N-t-butoxycarbonyl-S-trityl-L-penicillamyl-P-sulfophenylalanine (7.5 g).

In the same way the Compound D-28 listed in Table 1 described below was synthesized.

Reference Example 10 (Synthesis of the Compound C-23)

To the solution of tetrabutylammonium N-t-butoxycarbonyl-S-trityl-L-penicillamyl-p-sulfophenylalanine (B-23)(7.5 g) and 2,6-lutidine (3.8 ml) in dichloromethane (100 ml), was added dropwise at 0° C. the solution of trimethylsylyl trifluoromethanesulfonate (5.5 ml), and the mixture was stirred for 1 hour while the temperature was gradually returned to the room temperature. The solvent was evaporated off under reduced pressure and the residue was washed with diethyl ether and acetone, in this order, to give S-trityl-L-penicillamyl-p-sulfophenylalanine (3.1g).

Table 1 shows the structure, physical properties, and NMR data of the Compounds A-1 to F-32 synthesized in the Reference Examples.

TABLE 1

$$\underset{X-Pen-Y}{\overset{Z}{|}}$$

| Compound | X | Configuration of Pen | Y | Z | Molecular formula Physical properties | Related Ref. Ex. | NMR spectra TMS internal standard (δ, ppm) in CDCl₃ |
|---|---|---|---|---|---|---|---|
| A-1 | Boc | L | OH | Trt | $C_{29}H_{33}NO_4S$ amorphous | 1 | 1.07(3H), 1.13(3H), 1.44(9H), 3.41(1H), 5.32(1H), 7.14-7.34 (9H), 7.50-7.70(6H), 8.20(1H) |
| A-2 | Boc | D | OH | Trt | $C_{29}H_{33}NO_4S$ amorphous | 1 | 1.06(3H), 1.12(3H), 1.44(9H), 3.46(1H), 4.90(1H), 5.37(1H), 7.10-7.36(9H), 7.56-7.70 (6H) |
| B-1 | Boc | D | OMe | Trt | $C_{30}H_{35}NO_4S$ amorphous | 2 | 1.02(2H), 1.07(3H), 1.45(9H), 3.54(1H), 3.36(3H), 5.37(1H), 7.10-7.33(9H), 7.53-7.70 (6H) |
| B-2 | Boc | L | Gly—OEt | Trt | $C_{33}H_{40}N_2O_5S$ amorphous | 3 | 1.11(3H), 1.18(3H), 1.25(3H), 1.42(9H), 3.22(1H), 3.96(2H), 4.17(2H), 5.34(1H), 6.20(1H), 7.14-7.34(9H), 7.57-7.70(6H) |
| B-3 | Boc | D | Gly—OEt | Trt | $C_{33}H_{40}N_2O_5S$ amorphous | 3 | 1.10(3H), 1.13(3H), 1.22(3H), 1.42(9H), 3.43(1H), 3.95(2H), 4.14(2H), 5.47(1H), 6.53(1H), 7.11-7.34(9H), 7.57-7.70(6H) |
| B-4 | Boc | L | L—Ala—OEt | Trt | $C_{34}H_{42}N_2O_5S$ amorphous | 3 | 1.06(3H), 1.13(3H), 1.24(3H), 1.38(3H), 1.43(9H), 3.38(1H), 4.15(1H), 4.49(1H), 5.36(1H), 6.38(1H), 7.14-7.40(9H), 7.56-7.70(6H) |
| B-5 | Boc | L | L—Val—OMe | Trt | $C_{35}H_{44}N_2O_5S$ amorphous | 3 | 0.88(3H), 0.92(3H), 1.05(3H), 1.16(3H), 1.42(9H), 2.13(1H), 3.31(1H), 3.66(3H), 4.47(1H), 5.33(1H), 6.34(1H), 7.15-7.38 (9H), 7.55-7.73(6H) |
| B-6 | Boc | D | L—Val—OMe | Trt | $C_{35}H_{44}N_2O_5S$ amorphous | 3 | 0.87(3H), 0.90(3H), 1.05(3H), 1.17(3H), 1.43(9H), 2.12(1H), 3.29(1H), 3.70(3H), 4.48(1H), 5.34(1H), 6.37(1H), 7.16-7.38 (9H), 7.58-7.68(6H) |
| B-7 | Boc | L | L—Leu—OEt | Trt | $C_{37}H_{48}N_2O_5S$ amorphous | 3 | 0.91(6H), 1.02(3H), 1.14(3H), 1.22(3H), 1.42(9H), 1.30-1.80 (3H), 3.45(1H), 4.13(2H), 4.55 (1H), 5.33(1H), 6.23(1H), 7.10-7.40(9H), 7.50-7.75(6H) |
| B-8 | Boc | L | L—Pro—OMe | Trt | $C_{35}H_{42}N_2O_5S$ amorphous | 3 | 1.12(3H), 1.14(3H), 1.44(9H), 1.82-2.32(4H), 3.27-3.66(2H), 3.64(3H), 3.97(1H), 4.47(1H), 5.40(1H), 7.12-7.33(9H), 7.56-7.66(6H) |
| B-9 | Boc | L | L—Phe—OEt | Trt | $C_{40}H_{46}N_2O_5S$ amorphous | 3 | 1.03(3H), 1.09(3H), 1.16(3H), 1.43(9H), 3.07(2H), 3.20(1H), 4.09(2H), 4.81(1H), 5.29(1H), 6.29(1H), 7.04-7.38(14H), 7.52-7.73(6H) |
| B-10 | Boc | L | L—Tyr—OEt | Trt | $C_{40}H_{46}N_2O_6S$ amorphous | 3 | 1.02(3H), 1.07(3H), 1.18(3H), 1.44(9H), 2.98(2H), 3.26(1H), 4.09(2H), 4.75(1H), 5.39(1H), 5.87(1H), 6.63(2H), 6.94(2H), 7.12-7.32(10H), 7.55-7.64(6H) |
| B-11 | Boc | L | L—Glu⟨OEt, OEt | Trt | $C_{38}H_{48}N_2O_7S$ amorphous | 3 | 1.04(3H), 1.17(3H), 1.24(6H), 1.43(9H), 1.80-2.50(4H), 3.23 (1H), 4.09(2H), 4.15(2H), 4.54 (1H), 5.32(1H), 6.38(1H), 7.13-7.34(9H), 7.57-7.67(6H) |
| B-12 | Boc | L | NHCHPh₂ | Trt | $C_{42}H_{44}N_2O_3S$ m.p. 158.0-159.0 | 3 | 0.98(3H), 1.15(3H), 1.41(9H), 3.60(1H), 5.29(1H), 6.15(1H), 6.41(1H), 7.12-7.34(9H), 7.48-7.58(6H) |
| B-13 | Boc | L | L—Asp⟨OBzl, OBzl | Trt | $C_{47}H_{50}N_2O_7S$ amorphous | 3 | 1.05(3H), 1.12(3H), 1.41(9H), 2.85(1H), 2.94(2H), 4.80(1H), 5.02(2H), 5.07(2H), 5.25(1H), 6.11(1H), 7.12-7.40(19H), 7.56-7.67(6H) |
| B-14 | Boc | L | L—Met—OEt | Trt | $C_{36}H_{46}N_2O_5S_2$ | 3 | 1.06(3H), 1.17(3H), 1.24(3H), |

TABLE 1-continued $$\begin{array}{c} Z \\ | \\ X-Pen-Y \end{array}$$

| Compound | X | Configuration of Pen | Y | Z | Molecular formula Physical properties | Related Ref. Ex. | NMR spectra TMS internal standard (δ, ppm) in CDCl₃ |
|---|---|---|---|---|---|---|---|
| | | | | | amorphous | | 1.43(9H), 1.25-2.24(2H), 2.05(3H), 2.50(2H), 3.22(1H), 4.16(2H), 4.61(1H), 5.31(1H), 6.40(1H), 7.15-7.40(9H), 7.57-7.67(6H) |
| B-15 | Boc | L | L—Ile—OMe | Trt | $C_{36}H_{46}N_2O_5S$ amorphous | 3 | 0.89(6H), 1.03(3H), 1.16(3H), 1.35-1.52(2H), 1.42(9H), 1.86(1H), 3.34(1H), 3.66(3H), 4.52(1H), 5.32(1H), 6.38(1H), 7.15-7.42(9H), 7.53-7.73(6H) |
| B-16 | Boc | D | NHCHPh₂ | Trt | $C_{42}H_{44}N_2O_3S$ m.p. 158.0–159.0 | 3 | 0.98(3H), 1.15(3H), 1.41(9H), 3.60(1H), 5.28(1H), 6.15(1H), 6.40(1H), 7.10-7.40(19H), 7.48-7.57(6H) |
| B-17 | Boc | D | L—Leu—OEt | Trt | $C_{37}H_{48}N_2O_5S$ amorphous | 3 | 0.82-0.91(6H), 1.05(3H), 1.15(3H), 1.24(3H), 1.42(9H), 1.30-1.81(3H), 3.34(1H), 4.14(2H), 4.51(1H), 5.33 (1H), 6.13(1H), 7.15-7.33(9H), 7.56-7.63(6H) |
| B-18 | Boc | D | L—Phe—OEt | Trt | $C_{40}H_{46}N_2O_5S$ amorphous | 3 | 0.99(3H), 1.11(3H), 1.14(3H), 1.42(9H), 2.93-3.16(2H), 3.34(1H), 4.08(2H), 4.77(1H), 5.27(1H), 6.32(1H), 7.08-7.33(14H), 7.54-7.63(6H) |
| B-19 | Boc | D | ┌—OEt<br>L—Glu—OEt | Trt | $C_{38}H_{48}N_2O_7S$ amorphous | 3 | 1.08(3H), 1.17(3H), 1.20(3H), 1.25(3H), 1.42(9H), 1.82-2.43(4H), 3.20(1H), 4.07(2H), 4.16(2H), 4.53(1H), 5.34(1H), 6.39(1H), 7.15-7.36(9H), 7.56-7.68(6H) |
| B-20 | Boc | L | L—Ser—OMe | Trt | $C_{34}H_{40}N_2O_6S$ amorphous | 3 | 1.12(3H), 1.34(3H), 1.41(9H), 2.06(1H), 3.68-4.10(2H), 3.76(3H), 4.38(1H), 5.21(1H), 6.06(1H), 7.19-7.38(10H), 7.63-7.73(6H) |
| B-21 | Boc | D | L—Pro—OMe | Trt | $C_{35}H_{42}N_2O_5S$ amorphous | 3 | 0.94(6H), 1.45(9H), 1.80-2.22(4H), 3.43-3.91(2H), 3.70(3H), 4.38-4.49 (2H), 5.43(1H), 7.10-7.32(9H), 7.51-7.63(6H) |
| B-22 | Boc | L | CH₂COOEt<br>\|<br>Tyr—OEt | Trt | $C_{44}H_{52}N_2O_8S$ amorphous | 3 | 1.03(3H), 1.10(3H), 1.17(3H), 1.30(3H), 1.43(9H), 3.00(2H), 3.16(1H), 4.07(2H), 4.27(2H), 4.58(2H), 4.73(1H), 5.29(1H), 6.27(1H), 6.78(2H), 7.05(2H), 7.12-7.30(9H), 7.55-7.64(6H) |
| B-23 | Boc | L | SO₃·Bu₄N<br>\|<br>DL—Phe—OH | Trt | $C_{54}H_{77}N_3O_8S_2$ amorphous | 9 | 0.92(12H), 1.05(3H), 1.07(3H) 1.23-1.66(16H), 1.43(9H), 3.02-3.26(1H), 4.62-4.75(1H), 5.36-5.45(1H), 6.37(1H), 7.10-7.43(12H), 7.56-7.78(8H) |
| C-1 | H | D | OMe | Trt | $C_{25}H_{27}NO_2S$ oily | 4 | 1.07(3H), 1.11(3H), 1.63(2H), 2.33(1H), 3.54(3H), 7.12-7.32 (9H), 7.56-7.68(6H) |
| C-2 | H | L | Gly—OEt | Trt | $C_{28}H_{32}N_2O_3S$ amorphous | 4 | 1.24(3H), 1.27(3H), 1.29(3H), 1.64(2H), 1.81(2H), 3.87(2H), 4.16(2H), 6.95(1H), 7.13-7.34 (9H), 7.63-7.73(6H) |
| C-3 | H | D | Gly—OEt | Trt | $C_{28}H_{32}N_2O_3S$ amorphous | 4 | 1.25(3H), 1.27(3H), 1.29(3H), 1.62(2H), 1.80(1H), 3.88(2H), 4.16(2H), 6.96(1H), 7.16-7.37 (9H), 7.62-7.73(6H) |
| C-4 | H | L | L—Ala—OEt | Trt | $C_{29}H_{34}N_2O_3S$ amorphous | 4 | 1.23(3H), 1.24(3H), 1.26(3H), 1.30(3H), 1.62(2H), 1.78(1H), 4.14(2H), 4.39(1H), 6.84(1H), 7.15-7.36(9H), 7.63-7.73(6H) |
| C-5 | H | L | L—Val—OMe | Trt | $C_{30}H_{36}N_2O_3S$ amorphous | 4 | 0.84(3H), 0.87(3H), 1.25(3H), 1.26(3H), 1.64(2H), 1.79(1H), 2.10(1H), 3.68(3H), 4.36(1H), 6.80(1H), 7.14-7.34(9H), 7.62-7.73(6H) |
| C-6 | H | D | L—Val—OMe | Trt | $C_{30}H_{36}N_2O_3S$ | 4 | 0.83(3H), 0.86(3H), 1.24(3H), |

TABLE 1-continued $$X-Pen-Y \text{ with } Z$$

| Compound | X | Configuration of Pen | Y | Z | Molecular formula Physical properties | Related Ref. Ex. | NMR spectra TMS internal standard (δ, ppm) in CDCl₃ |
|---|---|---|---|---|---|---|---|
| | | | | | amorphous | | 1.29(3H), 1.80(1H), 2.06(1H), 2.09(2H), 3.69(3H), 4.31(1H), 6.67(1H), 7.16-7.36(9H), 7.64-7.73(6H) |
| C-7 | H | L | L—Leu—OEt | Trt | C₃₂H₄₀N₂O₃S amorphous | 4 | 0.80-1.00(6H), 1.23(6H), 1.24 (3H), 1.35-1.73(3H), 1.65(2H), 1.84(1H), 4.12(2H), 4.36-4.49 (1H), 6.73(1H), 7.14-7.35(9H), 7.61-7.73(6H) |
| C-8 | H | L | L—Pro—OMe | Trt | C₃₀H₃₄N₂O₃S amorphous | 4 | 1.29(3H), 1.34(3H), 1.60-2.22 (4H), 1.84(2H), 2.61(1H), 2.96 (2H), 3.63(3H), 4.35(1H), 7.05-7.42(9H), 7.50-7.78(6H) |
| C-9 | H | L | L—Phe—OEt | Trt | C₃₅H₃₈N₂O₃S amorphous | 4 | 1.08(3H), 1.18(3H), 1.19(3H), 1.58(2H), 1.62(1H), 3.00(2H), 4.11(2H), 4.69(1H), 6.67(1H), 7.01-7.38(14H), 7.59-7.70(6H) |
| C-10 | H | L | L—Tyr—OEt (with SiMe₃) | Trt | C₃₅H₄₆N₂O₄SSi amorphous | 4 | 0.26(9H), 1.09(3H), 1.18(6H), 1.60(2H), 1.63(1H), 2.93(2H), 4.10(1H), 4.64(1H), 6.67(1H), 6.75(2H), 6.95(2H), 7.10-7.38 (9H), 7.60-7.70(6H) |
| C-11 | H | L | L—Glu—OEt (with —OEt) | Trt | C₃₃H₄₀N₂O₅S amorphous | 4 | 1.23(6H), 1.24(6H), 1.64(2H), 1.84(1H), 1.80-2.43(4H), 4.10 (2H), 4.14(2H), 4.42(1H), 6.98 (1H), 7.15-7.36(9H), 7.63-7.72 (6H) |
| C-12 | H | L | NHCHPh₂ | Trt | C₃₇H₃₆N₂OS amorphous | 4 | 1.20(3H), 1.21(3H), 1.62(2H), 1.97(1H), 6.07(1H), 7.10-7.32 (20H), 7.60-7.70(6H) |
| C-13 | H | L | L—Asp—OBzl (with —OBzl) | Trt | C₄₂H₄₂N₂O₅S amorphous | 4 | 1.17(6H), 1.50(1H), 1.58(2H), 2.72(1H), 3.04(1H), 4.76(1H), 4.96-5.17(4H), 6.91(1H), 7.08-7.44(19H), 7.55-7.77(6H) |
| C-14 | H | L | L—Met—OEt | Trt | C₃₁H₃₈N₂O₃S₂ amorphous | 4 | 1.12-1.34(9H), 1.63(2H), 1.84(1H), 1.80-2.20(2H), 2.05(3H), 2.44(2H), 4.16(2H), 4.52(1H), 7.01(1H), 7.13-7.42(9H), 7.56-7.79(6H) |
| C-15 | H | L | L—Ile—OMe | Trt | C₃₁H₃₈N₂O₃S amorphous | 4 | 0.73-0.94(6H), 0.96-1.93(3H), 1.04(3H), 1.17(3H), 1.61(2H), 1.79(1H), 3.68(3H), 4.41(1H), 6.82(1H), 7.14-7.38(9H), 7.56-7.74(6H) |
| C-16 | H | D | NHCHPh₂ | Trt | C₃₇H₃₆N₂OS amorphous | 4 | 1.21(3H), 1.22(3H), 1.59(2H), 1.96(1H), 6.06(1H), 7.06-7.35 (19H), 7.53(1H), 7.58-7.68(6H) |
| C-17 | H | D | L—Leu—OEt | Trt | C₃₂H₄₀N₂O₃S amorphous | 4 | 0.88(6H), 1.23(3H), 1.25(3H), 1.28(3H), 1.40-1.74(3H), 1.61(2H), 1.88(1H), 4.13(2H), 4.38(1H), 6.81(1H), 7.15-7.37(9H), 7.57-7.72(6H) |
| C-18 | H | D | L—Phe—OEt | Trt | C₃₅H₃₈N₂O₃S amorphous | 4 | 1.17(3H), 1.20(3H), 1.23(3H), 1.48(2H), 1.71(1H), 3.00(2H), 4.10(2H), 4.65(1H), 6.88(1H), 7.00-7.36(14H), 7.67-7.72(6H) |
| C-19 | H | D | L—Glu—OEt (with —OEt) | Trt | C₃₃H₄₀N₂O₅S oily | 4 | 1.23(3H), 1.24(6H), 1.27(3H), 1.60(2H), 1.82(1H), 1.80-2.42(4H), 4.08(2H), 4.14(2H), 4.39(1H), 6.97(1H), 7.14-7.36(9H) 7.62-7.73(6H) |
| C-20 | H | L | L—Ser—OMe (with Si(Me)₃) | Trt | C₃₂H₄₀N₂O₄SSi amorphous | 4 | 0.08(9H), 1.27(3H), 1.29(3H), 1.62(2H), 1.67(1H), 3.61-3.98(2H), 3.68(3H), 4.50(1H), 6.79(1H), 7.15-7.37(9H), 7.65-7.74(6H) |
| C-21 | H | D | L—Pro—OMe | Trt | C₃₀H₃₄N₂O₃S | 4 | 1.05(3H), 1.31(3H), 1.60-2.12(4H), |

TABLE 1-continued $$X-Pen-Y$$
with Z on Pen

| Compound | X | Configuration of Pen | Y | Z | Molecular formula Physical properties | Related Ref. Ex. | NMR spectra TMS internal standard (δ, ppm) in CDCl₃ |
|---|---|---|---|---|---|---|---|
|  |  |  |  |  | amorphous |  | 1.82(2H), 2.90(1H), 2.90-3.32(2H), 3.68(3H), 4.25-4.32(1H), 7.12-7.34(9H), 7.57-7.68(6H) |
| C-22 | H | L | CH₂COOEt \| Tyr—OEt | Trt | C₃₉H₄₄N₂O₆S amorphous | 4 | 1.09(3H), 1.18(3H), 1.20(3H), 1.31(3H), 1.55(2H), 1.64(1H), 2.95(2H), 4.11(2H), 4.28(2H), 4.60(2H), 4.53-4.76(1H), 6.69(1H), 6.82(2H), 7.01(2H), 7.07-7.31(9H), 7.58-7.69(6H) |
| C-23 | H | L | SO₃H \| DL—Phe—OH | Trt | C₃₃H₃₄N₂O₆S₂ amorphous | 10 | *0.99(3H), 1.11(3H), 2.09(2H), 2.10(1H), 3.01(2H), 4.39(1H), 7.16-8.52(22H) |
| D-1 | Boc—L—Glu—OBzl | D | OMe | Trt | C₄₂H₄₅N₂O₇S amorphous | 6 | 1.01(3H), 1.12(3H), 1.41(9H), 1.70-2.45(4H), 3.65(3H), 3.85(1H), 4.35(1H), 5.16(2H), 5.34(1H), 6.54(1H), 7.13-7.37(14H), 7.54-7.62(6H) |
| D-2 | Boc—D—Glu—OMe | D | OMe | Trt | C₃₆H₄₄N₂O₇S amorphous | 6 | 1.02(3H), 1.13(3H), 1.44(9H), 1.70-2.45(4H), 3.68(3H), 3.72(3H), 3.81(1H), 4.33(1H), 5.29(1H), 6.38(1H), 7.14-7.32(9H), 7.53-7.68(6H) |
| D-3 | Ac | L | Gly—OEt | Trt | C₃₀H₃₄N₂O₄S amorphous | 5 | 1.11(3H), 1.15(3H), 1.25(3H), 1.98(3H), 3.77(1H), 3.95(2H), 4.18(2H), 6.23-6.36(2H), 7.16-7.35(9H), 7.58-7.67(6H) |
| D-4 | Boc—L—Glu—OBzl | L | Gly—OEt | Trt | C₄₅H₅₃N₃O₈S amorphous | 6 | 1.12(3H), 1.19(3H), 1.25(3H), 1.41(9H), 1.55-2.26(4H), 3.57(1H), 3.94(2H), 4.17(2H), 4.33(1H), 5.12(2H), 5.38(1H), 6.23(1H), 6.36(1H), 7.14-7.44(14H), 7.54-7.76(6H) |
| D-5 | Boc—L—Glu—OBzl | D | Gly—OEt | Trt | C₄₅H₅₃N₃O₈S amorphous | 6 | 1.13(3H), 1.17(3H), 1.21(3H), 1.39(9H), 1.52-2.32(4H), 3.65(1H), 3.91(2H), 4.12(2H), 4.29(1H), 5.14(2H), 5.46(1H), 6.52(1H), 6.87(1H), 7.10-7.44(14H), 7.46-7.76(6H) |
| D-6 | Boc—D—Glu—OMe | D | Gly—OEt | Trt | C₃₉H₄₉N₃O₈S amorphous | 6 | 1.12(3H), 1.20(3H), 1.25(3H), 1.42(9H), 1.48-2.36(4H), 3.63(1H), 3.68(3H), 3.94(2H), 4.17(2H), 4.30(1H), 5.34(1H), 6.26(1H), 6.48(1H), 7.15-7.34(9H), 7.57-7.67(6H) |
| D-7 | Boc—L—Glu—OBzl | L | Gly—OEt | Trt | C₄₅H₅₃N₃O₈S amorphous | 6 | 1.12(3H), 1.15(3H), 1.24(3H), 1.40(9H), 1.80-2.20(2H), 2.35-2.63(2H), 3.51(1H), 3.92(2H), 4.10(1H), 4.15(2H), 5.10(2H), 5.34(1H), 6.34(1H), 6.94(1H), 7.14-7.37(14H), 7.58-7.67(6H) |
| D-8 | Boc—L—Asp—OBzl | D | Gly—OEt | Trt | C₄₄H₅₁N₃O₈S amorphous | 6 | 1.10(3H), 1.18(3H), 1.24(3H), 1.39(9H), 2.62-2.96(2H), 3.51(1H), 3.90(2H), 4.12(2H), 4.52(1H), 5.14(2H), 5.74(1H), 6.20-6.35(2H), 7.14-7.35(14H), 7.56-7.66(6H) |
| D-9 | Boc—L—Glu—OBzl | L | L—Ala—OEt | Trt | C₄₆H₅₅N₃O₈S amorphous | 6 | 1.09(3H), 1.15(3H), 1.23(3H), 1.34(3H), 1.42(9H), 1.65-2.28(4H), 3.61(1H), 4.14(2H), 4.33(1H), 4.44(1H), 5.12(2H), 5.38(1H), 6.24(1H), 6.38(1H), 7.14-7.44(14H), 7.58-7.68(6H) |

TABLE 1-continued $$X-Pen-Y$$
$$\overset{Z}{|}$$

| Compound | X | Configuration of Pen | Y | Z | Molecular formula Physical properties | Related Ref. Ex. | NMR spectra TMS internal standard (δ, ppm) in CDCl$_3$ |
|---|---|---|---|---|---|---|---|
| D-10 | Boc—L—Glu—OBzl (with bracket) | L | L—Val—OMe | Trt | C$_{47}$H$_{5-}$N$_3$O$_8$S amorphous | 6 | 0.85(3H), 0.89(3H), 1.12(3H), 1.21 (3H), 1.42(9H), 1.70-2.28(5H), 3.39(1H), 3.65(3H), 4.36(1H), 4.41 (1H), 5.09(2H), 5.46(1H), 6.19(1H), 6.46(1H), 7.15-7.41(14H), 7.59-7.69(6H) |
| D-11 | Boc—L—Glu—OBzl | D | L—Val—OMe | Trt | C$_{47}$H$_{5-}$N$_3$O$_8$S amorphous | 6 | 0.85(3H), 0.88(3H), 1.06(3H), 1.15 (3H), 1.39(9H), 1.60-2.37(5H), 3.68(3H), 3.76(1H), 4.26(1H), 4.44 (1H), 5.07-5.23(2H), 5.37(1H), 6.38 (1H), 6.49(1H), 7.15-7.44(14H), 7.56-7.66(6H) |
| D-12 | Boc—L—Glu—OBzl | L | L—Leu—OEt | Trt | C$_{49}$H$_{61}$N$_3$O$_8$S m.p. 177.0-179.0 | 6 | 0.85-0.97(6H), 1.10(3H), 1.18(3H), 1.22(3H), 1.42(9H), 1.30-2.27(7H), 3.61(1H), 4.11(2H), 4.34(1H), 4.44 (1H), 5.10(2H), 5.40(1H), 6.10(1H), 6.39(1H), 7.14-7.40(14H), 7.58-7.67(6H) |
| D-13 | Boc—L—Glu—OBzl | L | L—Pro—OEt | Trt | C$_{47}$H$_{55}$N$_3$O$_8$S amorphous | 6 | 1.22(3H), 1.26(3H), 1.42(9H), 1.67-2.34(8H), 3.06-3.20(1H), 3.40-3.52(1H), 3.63(3H), 3.93(1H), 4.37 (1H), 4.42(1H), 5.12(2H), 5.36(1H), 6.42(1H), 7.10-7.44(14H), 7.49-7.72(6H) |
| D-14 | Boc—L—Glu—OBzl | L | L—Phe—OEt | Trt | C$_{52}$H$_{59}$N$_3$O$_9$S amorphous | 6 | 1.08(3H), 1.13(3H), 1.26(3H), 1.42 (9H), 1.54-2.24(4H), 3.02(2H), 3.39(1H), 4.12(2H), 4.32(1H), 4.75 (1H), 5.12(2H), 5.46(1H), 6.20-6.38(2H), 7.03-7.38(19H), 7.53-7.63(6H) |
| D-15 | Boc—L—Glu—OBzl | L | SiMe$_3$<br>\|<br>L—Tyr—OEt | Trt | C$_{55}$H$_{67}$N$_3$O$_9$SSi amorphous | 6 | 0.26(9H), 1.09(3H), 1.15(6H), 1.43 (9H), 1.58-2.30(4H), 2.95(2H), 3.33 (1H), 4.06(2H), 4.33(1H), 4.70(1H), 5.12(2H), 5.49(1H), 6.23(1H), 6.32 (1H), 6.75(2H), 6.97(2H), 7.10-7.40 (14H), 7.55-7.65(6H) |
| D-16 | Boc—L—Glu—OBzl | L | ⎡—OEt<br>L—Glu—OEt | Trt | C$_{50}$H$_{61}$N$_3$O$_{10}$S m.p. 167.0-168.5 | 6 | 1.08(3H), 1.18(3H), 1.22(3H), 1.26 (3H), 1.42(9H), 1.80-2.42(8H), 3.49(1H), 4.10(2H), 4.12(2H), 4.34 (1H), 4.48(1H), 5.11(2H), 5.41(1H), 6.30(1H), 6.40(1H), 7.15-7.37 (14H), 7.57-7.69(6H) |
| D-17 | Boc—L—Glu—OBzl | L | NHCHPh$_2$ | Trt | C$_{54}$H$_{57}$N$_3$O$_6$S amorphous | 6 | 1.07(3H), 1.16(3H), 1.41(9H), 1.68-2.23(4H), 3.89(1H), 4.31(1H), 5.10(2H), 5.36(1H), 6.09(1H), 6.28-6.43(2H), 7.10-7.36(24H), 7.50-7.58(6H) |
| D-18 | Boc—L—Glu—OBzl | L | ⎡—OBzl<br>L—Asp—OBzl | Trt | C$_{59}$H$_{63}$N$_3$O$_{10}$S amorphous | 6 | 1.07(3H), 1.19(3H), 1.41(9H), 1.70-2.27(4H), 2.72-3.12(2H), 2.96(1H), 4.32(1H), 4.80(1H), 4.94-5.22(6H), 5.43(1H), 6.25(1H), 6.52(1H), 7.03-7.44(24H), 7.56-7.64(6H) |
| D-19 | Boc—L—Glu—OBzl | L | L—Met—OEt | Trt | C$_{48}$H$_{59}$N$_3$O$_8$S$_2$ m.p. 161.5-163.0 | 6 | 1.11(3H), 1.21(3H), 1.23(3H), 1.43(9H), 1.72-2.28(6H), 2.05(3H), 2.47(2H), 3.38(1H), 4.15(2H), 4.34(1H), 4.56(1H), 4.97-5.23(2H), 5.42(1H), 6.25(1H), 6.39(1H), 7.14-7.37(14H), 7.58-7.67(6H) |

TABLE 1-continued $$X-\underset{\underset{Z}{|}}{Pen}-Y$$

| Compound | X | Configuration of Pen | Y | Z | Molecular formula Physical properties | Related Ref. Ex | NMR spectra TMS internal standard (δ, ppm) in CDCl₃ |
|---|---|---|---|---|---|---|---|
| D-20 | Boc—L—Glu—OBzl | L | L—Ile—OMe | Trt | $C_{48}H_{59}N_3O_8S$ m.p. 159.5-160.5 | 6 | 0.76-0.96(6H), 1.00-1.59(2H), 1.11(3H), 1.20(3H), 1.43(9H), 1.71-2.30(5H), 3.43(1H), 3.65(3H), 4.36(1H), 4.44(1H), 4.95-5.22(2H), 5.44(1H), 6.28(1H), 6.45(1H), 7.08-7.42(14H), 7.52-7.76(6H) |
| D-21 | Boc—L—Glu—OBzl | D | NHCHPh₂ | Trt | $C_{54}H_{57}N_3O_6S$ amorphous | 6 | 1.00(3H), 1.15(3H), 1.36(9H), 1.53-2.26(4H), 3.98(1H), 4.03(1H), 5.12(2H), 5.33(1H), 6.15(1H), 6.56(1H), 6.89(1H), 7.08-7.36(24H), 7.50-7.58(6H) |
| D-22 | Boc—L—Glu—OBzl | D | L—Leu—OEt | Trt | $C_{49}H_{61}N_3O_8S$ amorphous | 6 | 0.76-0.90(6H), 1.09(3H), 1.54(3H), 1.22(3H), 1.30-2.32(7H), 1.39(9H), 3.67(1H), 4.11(2H), 4.24(1H), 4.50(1H), 5.14(2H), 5.32(1H), 6.30(1H), 6.40(1H), 7.14-7.37(14H), 7.55-7.64(6H) |
| D-23 | Boc—L—Glu—OBzl | D | L—Phe—OEt | Trt | $C_{52}H_{59}N_3O_8S$ amorphous | 6 | 1.02(3H), 1.12(6H), 1.40(9H), 1.60-2.29(4H), 3.03(2H), 3.62(1H), 4.06(2H), 4.24(1H), 4.73(1H), 5.14(2H), 5.36(1H), 6.31(1H), 6.54(1H), 7.06-7.40(19H), 7.65-7.64(6H) |
| D-24 | Boc—L—Glu—OBzl | D | L—Glu(—OEt)—OEt | Trt | $C_{50}H_{61}N_3O_{10}S$ amorphous | 6 | 1.11(3H), 1.19(6H), 1.22(3H), 1.39(9H), 1.52-2.42(8H), 3.51(1H), 4.03(2H), 4.12(2H), 4.24(1H), 4.50(1H), 5.14(2H), 5.32(1H), 6.31(1H), 6.71(1H), 7.14-7.36(14H), 7.56-7.65(6H) |
| D-25 | Boc—L—Glu—OBzl | L | L—Ser(Si(Me)₃)—OMe | Trt | $C_{48}H_{61}N_3O_9SSi$ amorphous | 6 | 0.04(9H), 1.15(3H), 1.16(3H), 1.42(9H), 1.60-2.26(4H), 3.48(1H), 3.65(3H), 3.86(1H), 4.00(1H), 4.31(1H), 4.54(1H), 5.11(2H), 5.40(1H), 6.32(1H), 6.58(1H), 7.13-7.36(14H), 7.59-7.69(6H) |
| D-26 | Boc—L—Glu—OBzl | D | L—Pro—OMe | Trt | $C_{47}H_{55}N_3O_8S$ amorphous | 6 | 0.97(6H), 1.39(9H), 1.63-2.50(8H), 3.44-3.68(1H), 3.64(3H), 3.71-3.85(1H), 4.28(1H), 4.42(1H), 4.77(1H), 5.15(2H), 5.36(1H), 6.39(1H), 7.12-7.36(14H), 7.50-7.62(6H) |
| D-27 | Boc—L—Glu—OBzl | L | Tyr(—CH₂COOEt)—OEt | Trt | $C_{56}H_{65}N_3O_{11}S$ amorphous | 6 | 1.08(3H), 1.15(3H), 1.17(3H), 1.30(3H), 1.42(9H), 1.63-2.28(4H), 2.97(2H), 3.39(1H), 4.76(2H), 4.27(2H), 4.32(1H), 4.59(2H), 4.71(1H), 5.12(2H), 5.46(1H), 6.23(1H), 6.31(1H), 6.81(2H), 7.03(2H), 7.10-7.42(14H), 7.54-7.66(6H) |
| D-28 | Boc—L—Glu—OBzl | L | DL—Phe(—SO₃·Bu₄N)—OH | Trt | $C_{66}H_{90}N_4O_{11}S_2$ amorphous | 9 | *0.72(3H), 0.80(3H), 0.94(12H), 1.22-2.40(20H), 1.36(9/2H), 1.37(9/2H), 2.80-3.50(10H), 4.04(1H), 4.39(1H), 4.50(1H), 5.12(2H), 7.09-8.07(28H) |
| D-29 | Boc—L—Asp—OBzl | L | Gly—OEt | Trt | $C_{44}H_{51}N_3O_8S$ amorphous | 6 | 1.09(3H), 1.19(3H), 1.27(3H), 1.41(9H), 2.64-2.93(2H), 3.48(1H), 3.94(2H), 4.17(2H), 4.55(1H), 5.12(2H), 5.66(1H), 6.14-6.33(2H), 7.10-7.32(14H), 7.52-7.64(6H) |
| D-30 | Boc—L—Glu—OBzl | L | OH | Trt | $C_{41}H_{46}N_2O_7S$ amorphous | 3 | 1.08(3H), 1.18(3H), 1.42(9H), 1.83-2.32(4H), 3.63-3.72(1H), 4.34(1H), 5.12(2H), 5.39(1H), 6.49(1H), 7.10-7.43(15H), 7.48-7.56(6H) |
| E-1 | Boc | D | Gly—OH | Trt | $C_{31}H_{36}N_2O_5S$ | 7 | 1.04(3H), 1.06(3H), 1.43(9H), 3.73 |

TABLE 1-continued $$X-\underset{|}{\overset{Z}{Pen}}-Y$$

| Compound | X | Configuration of Pen | Y | Z | Molecular formula Physical properties | Related Ref. Ex. | NMR spectra TMS internal standard (δ, ppm) in CDCl₃ |
|---|---|---|---|---|---|---|---|
| | | | | | amorphous | | (1H), 4.00(2H), 5.69(2H), 6.68(1H), 7.10-7.33(9H), 7.54-7.64(6H), 8.28(1H) |
| E-2 | Boc—L—Glu—OH | D | OH | Trt | C₃₄H₄₀N₂O₇S amorphous | 7 | 0.97(6H), 1.37(9H), 1.80-2.62(4H), 4.18-4.90(3H), 5.69(1H), 6.83(1H), 7.12-7.30(9H), 7.46-7.61(6H), 8.06(1H) |
| E-3 | Boc—D—Glu—OH | D | OH | Trt | C₃₄H₄₀N₂O₇S amorphous | 7 | 0.96(6H), 1.36(9H), 1.82-2.53 (4H), 4.20-4.85(3H), 5.68(1H), 6.81(1H), 7.13-7.32(9H), 7.49-7.63(6H), 8.09(1H) |
| E-4 | Ac | L | Gly—OH | Trt | C₂₈H₃₀N₂O₄S amorphous | 7 | 1.08(3H), 1.11(3H), 1.97(3H), 3.89(1H), 3.97(2H), 6.51(1H), 6.62(1H), 7.12-7.38(9H), 7.54-7.67(6H), 7.00-8.00(1H) |
| E-5 | Boc—L—Glu—OH | L | Gly—OH | Trt | C₃₆H₄₃N₃O₈S amorphous | 7 | 0.89(3H), 0.97(3H), 1.45(9H), 1.71-2.80(4H), 3.47-3.70(2H), 4.20-4.73(2H), 5.07-5.50(2H), 7.06-7.27(9H), 7.47-7.64(6H), 8.05-9.00(3H) |
| E-6 | Boc—L—Glu—OH | D | Gly—OH | Trt | C₃₆H₄₃N₃O₈S amorphous | 7 | 1.05(3H), 1.06(3H), 1.39(9H), 1.76-2.56(4H), 3.66-4.34(4H), 6.64 (1H), 6.00-8.16(19H) |
| E-7 | Boc—D—Glu—OH | D | Gly—OH | Trt | C₃₆H₄₃N₃O₈S amorphous | 7 | 0.89(3H), 0.96(3H), 1.45(9H), 1.70-2.76(4H), 3.44-3.80(2H), 4.20-4.70(2H), 5.10-5.52(2H), 7.02-7.36(9H), 7.44-7.68(6H), 7.90-9.45(3H) |
| E-8 | Boc—L—Glu— | L | Gly—OH | Trt | C₃₆H₄₃N₃O₈S amorphous | 7 | *0.77(3H), 0.81(3H), 1.38(9H), 1.65-2.10(2H), 2.15-2.40(2H), 3.34(1H), 3.58-3.89(2H), 4.07 (1H), 4.40(1H), 6.80-7.88(16H), 7.77(1H), 8.42(1H), 12.28(1H) |
| E-9 | Boc—L—Asp—OH | D | Gly—OH | Trt | C₃₅H₄₁N₃O₈S amorphous | 7 | 0.98(3H), 1.06(3H), 1.34(9H), 2.64-3.08(2H), 3.60-4.70(4H), 5.90(1H), 6.90-7.30(11H), 7.44-7.66(6H), 9.54(2H) |
| E-10 | Boc—L—Glu—OH | L | L—Ala—OH | Trt | C₃₇H₄₅N₃O₈S amorphous | 7 | *0.78(3H), 0.82(3H), 1.26(3H), 1.39(9H), 1.60-2.54(4H), 3.33 (1H), 3.93(1H), 4.15(1H), 4.53 (1H), 7.04-7.38(10H), 7.49-7.59 (6H), 8.11(1H), 8.38(1H), 12.20 (1H) |
| E-11 | Boc—L—Glu—OH | L | L—Val—OH | Trt | C₃₉H₄₉N₃O₈S amorphous | 7 | 0.86(3H), 0.89(3H), 1.02(3H), 1.06(3H), 1.41(9H), 1.80-2.55 (5H), 4.06(1H), 4.24-4.48(2H), 5.68(1H), 7.07-7.33(10H), 7.43 (1H), 7.53-7.65(6H), 8.50(2H) |
| E-12 | Boc—L—Glu—OH | D | L—Val—OH | Trt | C₃₉H₄₉N₃O₈S amorphous | 7 | 0.87(3H), 0.90(3H), 1.04(3H), 1.08 (3H), 1.41(9H), 1.81-2.57(5H), 4.07(1H), 4.25-4.50(2H), 5.69(1H), 7.03-7.30(10H), 7.40(1H), 7.51-7.66(6H), 8.52(2H) |
| E-13 | Boc—L—Glu—OH | L | L—Leu—OH | Trt | C₄₀H₅₁N₃O₈S amorphous | 7 | *0.77-0.90(6H), 0.87(3H), 0.90 (3H), 1.39(9H), 1.30-2.12(5H), 2.36(2H), 3.68(1H), 3.94(1H), 4.22 (1H), 4.49(1H), 7.08-7.35(10H), 7.50-7.62(6H), 8.07(1H), 8.18(1H), 12.32(1H) |

TABLE 1-continued $$X-Pen-Y$$
with Z on Pen

| Compound | X | Configuration of Pen | Y | Z | Molecular formula Physical properties | Related Ref. Ex | NMR spectra TMS internal standard (δ, ppm) in CDCl₃ |
|---|---|---|---|---|---|---|---|
| E-14 | Boc—L—Glu—OH | L | L—Pro—OH | Trt | $C_{39}H_{47}N_3O_8S$ amorphous | 7 | *0.96(3H), 1.12(3H), 1.37(9H), 1.57-2.52(8H), 3.06-3.62(3H), 3.93(1H), 4.14(1H), 4.27(1H), 7.09(1H), 7.10-7.38(9H), 7.44-7.62(6H), 8.10(1H), 12.40(1H) |
| E-15 | Boc—L—Glu—OH | L | L—Phe—OH | Trt | $C_{43}H_{49}N_3O_8S$ amorphous | 7 | *0.72(3H), 0.79(3H), 1.39(9H), 1.66-2.12(2H), 2.20-2.36(2H), 2.79-3.12(2H), 3.84-4.05(1H), 4.42(1H), 4.47(1H), 7.06-7.34(15H), 7.48-7.60(6H), 7.97(1H), 8.32(1H), 12.50(2H) |
| E-16 | Boc—L—Glu—OH | L | L—Tyr—OH | Trt | $C_{43}H_{49}N_3O_9S$ amorphous | 7 | 1.00(6H), 1.43(9H), 1.80-2.50(4H), 2.77-3.17(2H), 3.84(1H), 4.26(1H), 4.70(1H), 5.74(1H), 6.57(1H), 6.71(2H), 6.83(1H), 6.94(2H), 7.09-7.38(9H), 7.53-7.63(6H), 6.50-9.90(3H) |
| E-17 | Boc—L—Glu—OH | L | L—Glu—OH | Trt | $C_{39}H_{47}N_3O_{10}S$ amorphous | 7 | 0.99(3H), 1.09(3H), 1.43(9H), 1.85-2.64(8H), 3.91(1H), 4.23(1H), 4.49(1H), 5.81(1H), 6.98(1H), 7.10-7.43(10H), 7.52-7.74(6H), 8.20-11.6(3H) |
| E-18 | Boc—L—Glu—OH | L | NHCHPh₂ | Trt | $C_{47}H_{51}N_3O_6S$ amorphous | 7 | 1.06(6H), 1.40(9H), 1.70-2.50(4H), 4.12(1H), 4.26(1H), 5.48(1H), 6.06(1H), 6.61(1H), 6.94-7.34(20H), 7.46-7.55(6H), 6.90-8.00(1H) |
| E-19 | Boc—L—Glu—OH | L | L—Asp—OH | Trt | $C_{38}H_{45}N_3O_{10}S$ amorphous | 7 | *0.79(3H), 0.82(3H), 1.39(9H), 1.60-2.78(6H), 3.36(1H), 3.95(1H), 4.40-4.58(2H), 7.08-7.38(10H), 7.49-7.60(6H), 8.11(1H), 8.37(1H), 12.51(2H) |
| E-20 | Boc—L—Glu—OH | L | L—Met—OH | Trt | $C_{39}H_{49}N_3O_8S_2$ amorphous | 7 | *0.78(3H), 0.82(3H), 1.38(9H), 1.64-2.60(8H), 2.00(3H), 3.33(1H), 3.95(1H), 4.28(1H), 4.50(1H), 7.10-7.36(10H), 7.50-7.60(6H), 8.10(1H), 8.30(1H), 12.52(1H) |
| E-21 | Boc—L—Glu—OH | L | L—Ile—OH | Trt | $C_{40}H_{51}N_3O_8S$ amorphous | 7 | *0.70-0.90(12H), 1.02-1.54(2H), 1.38(9H), 1.66-2.10(3H), 2.22-2.42(2H), 3.32(1H), 3.93(1H), 4.11(1H), 4.54(1H), 7.11-7.37(10H), 7.48-7.60(6H), 8.00(1H), 8.08(1H), 12.42(1H) |
| E-22 | Boc—L—Glu—OH | D | NHCHPh₂ | Trt | $C_{47}H_{51}N_3O_6S$ m.p. 125.5-127.0 | 7 | 1.05(3H), 1.15(3H), 1.38(9H), 1.67-2.38(4H), 3.90(1H), 4.01(1H), 5.46(1H), 6.13(1H), 6.84(1H), 7.00-7.30(21H), 7.46-7.58(6H) |
| E-23 | Boc—L—Glu—OH | D | L—Leu—OH | Trt | $C_{40}H_{51}N_3O_8S$ amorphous | 7 | *0.63-0.92(12H), 1.25-2.03(5H), 1.38(9H), 2.14-2.56(2H), 3.34(1H), 3.88(1H), 4.22(1H), 4.54(1H), 7.04(1H), 7.15-7.36(9H), 7.47-7.59(6H), 8.14(1H), 8.42(1H), 12.44(1H) |
| E-24 | Boc—L—Glu—OH | D | L—Phe—OH | Trt | $C_{43}H_{49}N_3O_8S$ amorphous | 7 | *0.59(6H), 1.39(9H), 1.78-2.10(2H), 2.20-2.55(2H), 2.79-3.11(2H), 3.37(1H), 3.94(1H), 4.31-4.51(2H), 7.06-7.37(15H), 7.43-7.56(6H), 8.02(1H), 8.37(1H), 12.60(1H) |
| E-25 | Boc—L—Glu—OH | D | L—Glu—OH | Trt | $C_{39}H_{47}N_3O_{10}S$ amorphous | 7 | *0.74(3H), 0.80(3H), 1.39(9H), 1.62-2.08(4H), 2.12-2.54(4H), 3.35(1H), 3.88(1H), 4.24(1H), 4.53(1H), 7.04(1H), 7.11-7.37(9H), 7.47-7.60(6H), 8.02(1H), 8.46(1H), 12.34(2H) |

TABLE 1-continued $$X-Pen-Y \atop |\ Z$$

| Compound | X | Configuration of Pen | Y | Z | Molecular formula Physical properties | Related Ref. Ex. | NMR spectra TMS internal standard (δ, ppm) in CDCl$_3$ |
|---|---|---|---|---|---|---|---|
| E-26 | Boc—L—Glu—OH (cyclic) | L | L—Ser—OH | Trt | C$_37$H$_{45}$N$_3$O$_9$S amorphous | 7 | *0.80(3H), 0.85(3H), 1.39(9H), 1.62-2.12(2H), 2.22-2.53(2H), 3.34(2H), 3.56-3.77(2H), 3.93(1H), 4.24(1H), 4.54(1H), 7.06-7.35(10H), 7.48-7.61(6H), 8.10(1H), 8.19(1H), 12.44(1H) |
| E-27 | Boc—L—Glu—OH (cyclic) | D | L—Pro—OH | Trt | C$_{39}$H$_{47}$N$_3$O$_8$S amorphous | 7 | *0.85(3H), 0.88(3H), 1.38(9H), 1.65-2.46(8H), 3.33(1H), 3.30-3.70(2H), 3.75-3.97(1H), 4.20(1H), 4.80(1H), 6.99(1H), 7.14-7.17(9H), 7.43-7.55(6H), 8.17(1H), 12.42(1H) |
| E-28 | Boc—L—Glu—OH (cyclic) | L | CH$_2$COOH \| Tyr—OH | Trt | C$_{45}$H$_{51}$N$_3$O$_{11}$S amorphous | 7 | *0.75(3H), 0.81(3H), 1.39(9H), 1.60-2.14(2H), 2.21-2.46(2H), 2.75-3.02(2H), 3.35(1H), 3.98(1H), 4.37(1H), 4.48(1H), 4.60(2H), 6.75(2H), 7.04-7.38(12H), 7.50-7.62(6H), 8.03(1H), 8.27(1H), 12.67(2H) |
| E-29 | Boc—L—Glu—OH (cyclic) | L | SO$_3$·Bu$_4$N \| DL—Phe—OH | Trt | C$_{59}$H$_{84}$N$_4$O$_{11}$S$_2$ amorphous | 7 | *0.76(3H), 0.82(3H), 0.94(12H), 1.20-1.42(8H), 1.38(9H), 1.47-1.68(8H), 1.72-2.15(2H), 2.20-2.41(2H), 2.80-3.30(11H), 3.94(1H), 4.41(1H), 4.49(1H), 7.07-7.38(11H), 7.43-7.66(9H), 8.04(1H), 8.28(1H), 12.45(1H) |
| E-30 | Boc—L—Asp—OH (cyclic) | L | Gly—OH | Trt | C$_{39}$H$_{41}$N$_3$O$_8$S amorphous | 7 | 1.12(3H), 1.15(3H), 1.28(9H), 2.62-3.05(2H), 3.72-4.32(3H), 4.51(1H), 5.93(1H), 6.38-7.39(11H), 7.53-7.64(6H), 9.63(2H) |
| E-31 | Boc—L—Glu—OH (cyclic) | L | OH | Trt | C$_{34}$H$_{40}$N$_2$O$_7$S amorphous | 7 | *0.85(3H), 0.89(3H), 1.38(9H), 1.62-2.11(2H), 2.23-2.38(2H), 3.40(1H), 3.91(1H), 4.11(1H), 7.03(1H), 7.14-7.36(9H), 7.47-7.57(6H), 8.03(1H), 12.52(1H) |
| E-32 | Boc | L | Gly—OH | Trt | C$_{31}$H$_{36}$N$_2$O$_5$S$_2$ amorphous | 7 | 1.04(3H), 1.06(3H), 1.43(9H), 3.74(1H), 4.00(2H), 5.63(1H), 6.65(1H), 7.10-7.35(9H), 7.53-7.61(6H), 8.63(1H) |
| F-1 | H | D | Gly—OH | H | C$_7$H$_{14}$N$_2$O$_3$S·HCl 49-54° C. decomp. | 8 | **1.42(3H), 1.49(3H), 3.98(2H), 3.99(1H) |
| F-2 | H—L—Glu—OH (cyclic) | D | OH | H | C$_{10}$H$_{18}$N$_2$O$_5$S·HCl 84-89° C. decomp. | 8 | **1.38(3H), 1.43(3H), 2.01-2.22(2H), 2.45-2.59(2H), 3.93(1H), 4.43(1H) |
| F-3 | H—D—Glu—OH (cyclic) | D | OH | H | C$_{10}$H$_{18}$N$_2$O$_5$S·HCl 89-93° C. decomp. | 8 | **1.37(3H), 1.42(3H), 2.08-2.22(2H), 2.49-2.60(2H), 3.97(1H), 4.41(1H) |
| F-4 | Ac | L | Gly—OH | H | C$_9$H$_{16}$N$_2$O$_4$S 65-72° C. decomp. | 8 | **1.35(3H), 1.42(3H), 2.01(3H), 3.94(2H), 4.37(1H) |
| F-5 | H—L—Glu—OH (cyclic) | L | Gly—OH | H | C$_{12}$H$_{21}$N$_3$O$_6$S·HCl 121-125° C. decomp. | 8 | **1.35(3H), 1.41(3H), 2.06-2.21(2H), 2.41-2.69(2H), 3.93(2H), 3.97(1H), 4.38(1H) |
| F-6 | H—L—Glu—OH (cyclic) | D | Gly—OH | H | C$_{12}$H$_{21}$N$_3$O$_6$S·HCl 113-117° C. decomp. | 8 | **1.37(3H), 1.42(3H), 2.03-2.23(2H), 2.43-2.60(2H), 3.94(3H), 4.41(1H) |
| F-7 | H—D—Glu—OH (cyclic) | D | Gly—OH | H | C$_{12}$H$_{21}$N$_3$O$_6$S·HCl 127-131° C. decomp. | 8 | **1.35(3H), 1.41(3H), 2.07-2.21(2H), 2.41-2.67(2H), 3.93(2H), 3.96(1H), 4.38(1H) |
| F-8 | H—L—Glu— | L | Gly—OH | H | C$_{12}$H$_{21}$N$_3$O$_6$S·HCl 129-135° C. decomp. | 8 | **1.37(3H), 1.42(3H), 2.04-2.27(2H), 2.40-2.54(2H), 3.94(2H), 4.18(1H), 4.47(1H) |

TABLE 1-continued $$X-Pen\overset{\overset{Z}{|}}{-}Y$$

| Compound | X | Configuration of Pen | Y | Z | Molecular formula Physical properties | Related Ref. Ex. | NMR spectra TMS internal standard (δ, ppm) in CDCl$_3$ |
|---|---|---|---|---|---|---|---|
| F-9 | H—L—Asp—OH (bracket) | D | Gly—OH | H | C$_{11}$H$_{19}$N$_3$O$_6$S·HCl 130–134° C. decomp. | 8 | **1.35(3H), 1.40(3H), 2.89–3.17 (2H), 3.92(2H), 4.26(1H), 4.39(1H) |
| F-10 | H—L—Glu—OH (bracket) | L | L—Ala—OH | H | C$_{13}$H$_{24}$N$_3$O$_6$S·HCl 125–128° C. decomp. | 8 | **1.35(6H), 1.40(3H), 2.06–2.21 (2H), 2.40–2.66(2H), 3.97(1H), 4.28 (1H), 4.37(1H) |
| F-11 | H—L—Glu—OH | L | L—Val—OH | H | C$_{15}$H$_{27}$N$_3$O$_6$S·HCl 128–133° C. decomp. | 8 | **0.87(3H), 0.90(3H), 1.36(3H), 1.40 (3H), 1.98–2.30(3H), 2.38–2.70(2H), 3.98(1H), 4.13–4.23(1H), 4.46(1H) |
| F-12 | H—L—Glu—OH | D | L—Val—OH | H | C$_{15}$H$_{27}$N$_3$O$_6$S·HCl 119–124° C. decomp. | 8 | **0.89(3H), 0.92(3H), 1.34(3H), 1.39 (3H), 1.96–2.31(3H), 2.42–2.61(2H), 3.95(1H), 4.07–4.20(1H), 4.92(1H) |
| F-13 | H—L—Glu—OH | L | L—Leu—OH | H | C$_{16}$H$_{29}$N$_3$O$_6$S·HCl 114–119° C. decomp. | 8 | **0.78(3H), 0.84(3H), 1.35(3H), 1.40(3H), 1.53–1.72(3H), 2.03–2.17 (2H), 2.46–2.58(2H), 3.92(1H), 4.34 (1H), 4.38(1H) |
| F-14 | H—L—Glu—OH | L | L—Pro—OH | H | C$_{15}$H$_{25}$N$_3$O$_6$S·HCl 148–152° C. decomp. | 8 | **1.39(3H), 1.41(3H), 1.86–2.67 (8H), 3.80(2H), 3.97(1H), 4.35(1H) 4.60–4.80(1H) |
| F-15 | H—L—Glu—OH | L | L—Phe—OH | H | C$_{19}$H$_{27}$N$_3$O$_6$S·HCl 119–125° C. decomp. | 8 | **1.24(3H), 1.26(3H), 1.96–2.24 (2H), 2.28–2.58(2H), 2.82–3.29(2H), 3.97(1H), 4.30(1H), 4.69(1H), 7.13–7.32(5H) |
| F-16 | H—L—Glu—OH | L | L—Tyr—OH | H | C$_{19}$H$_{27}$N$_3$O$_7$S·HCl 133–139° C. decomp. | 8 | **1.24(3H), 1.26(3H), 1.98–2.24 (2H), 2.29–2.61(2H), 2.74–3.26(2H), 3.94(1H), 4.30(1H), 4.69(1H), 6.72 (2H), 7.05(2H) |
| F-17 | H—L—Glu—OH | L | L—Glu—OH | H | C$_{15}$H$_{25}$N$_3$O$_4$S·HCl 140–150° C. decomp. | 8 | **1.38(3H), 1.42(3H), 1.83–2.30(4H) 2.39–2.65(4H), 3.95(1H), 4.40(1H), 4.42(1H) |
| F-18 | H—L—Glu—OH | L | NHCHPh$_2$ | H | C$_{23}$H$_{29}$N$_3$O$_4$S·HCl 140–147° C. decomp. | 8 | *1.29(3H), 1.33(3H), 1.85–2.67(2H), 3.40(1H), 3.86(1H), 4.70(1H), 6.12 (1H), 7.12–7.43(10H), 8.20(1H), 8.50(1H), 9.13(1H) |
| F-19 | H—L—Glu—OH | L | L—Asp—OH | H | C$_{14}$H$_{23}$N$_3$O$_8$S·HCl 128–133° C. decomp. | 8 | **1.39(3H), 1.44(3H), 2.10–2.23 (2H), 2.51–2.62(2H), 2.94(2H), 3.97 (1H), 4.41(1H) |
| F-20 | H—L—Glu—OH | L | L—Met—OH | H | C$_{15}$H$_{26}$N$_3$O$_6$S$_2$·HCl 115–119° C. decomp. | 8 | **1.39(3H), 1.44(3H), 1.93–2.28 (4H), 2.04(3H), 2.41–2.70(4H), 4.00 (1H), 4.40(1H), 4.54(1H) |
| F-21 | H—L—Glu—OH | L | L—Ile—OH | H | C$_{16}$H$_{29}$N$_3$O$_6$S·HCl 121–126° C. decomp. | 8 | **0.83(3H), 0.89(3H), 1.05–1.56 (2H), 1.38(3H), 1.42(3H), 1.76–1.96 (1H), 2.06–2.30(2H), 2.43–2.72(2H), 4.01(1H), 4.25(1H), 4.47(1H) |
| F-22 | H—L—Glu—OH | D | NHCHPh$_2$ | H | C$_{23}$H$_{29}$N$_3$O$_4$S·HCl 120–125° C. decomp. | 8 | *1.30(3H), 1.35(3H), 1.96–2.15 (2H), 2.36–2.57(2H), 2.80(1H), 3.55 (2H), 3.85(1H), 4.72(1H), 6.14(1H), 7.12–7.48(10H), 8.19(1H), 8.49(2H), 9.12(1H) |
| F-23 | H—L—Glu—OH | D | L—Leu—OH | H | C$_{16}$H$_{29}$N$_3$O$_6$S·HCl 125–129° C. decomp. | 8 | **0.70–0.79(6H), 1.36(3H), 1.41 (3H), 1.50–1.82(3H), 2.06–2.31(2H), 2.42–2.68(2H), 4.01(1H), 4.33(1H), 4.43(1H) |

TABLE 1-continued $$\underset{X-Pen-Y}{\overset{Z}{|}}$$

| Compound | X | Configuration of Pen | Y | Z | Molecular formula Physical properties | Related Ref. Ex. | NMR spectra TMS internal standard (δ, ppm) in CDCl₃ |
|---|---|---|---|---|---|---|---|
| F-24 | H—L—Glu—OH | D | L—Phe—OH | H | $C_{19}H_{27}N_3O_6S \cdot HCl$ 126-129° C. decomp. | 8 | *1.13(3H), 1.18(3H), 1.90-2.13(2H), 2.41-2.66(2H), 2.58(1H), 2.41-2.58 (2H), 3.60(1H), 3.86(1H), 3.45(1H), 4.51(1H), 7.11-7.40(5H), 8.12(1H), 8.20-8.80(3H), 12.50(1H) |
| F-25 | H—L—Glu—OH | D | L—Glu—OH | H | $C_{15}H_{25}N_3O_4S \cdot HCl$ 120-123° C. decomp. | 8 | *1.33(3H), 1.37(3H), 1.65-2.13(4H), 2.26-2.39(2H), 2.40-2.57(2H), 2.79 (1H), 3.46(3H), 3.88(1H), 4.23(1H), 4.61(1H), 8.14(1H), 8.41(2H), 8.48 (1H), 12.10(1H) |
| F-26 | H—L—Glu—OH | L | L—Ser—OH | H | $C_{13}H_{23}N_3O_7S \cdot HCl$ 115-119° C. decomp. | 8 | *1.40(6H), 1.88-2.20(2H), 2.26-2.64 (2H), 2.79(1H), 3.40(2H), 3.58(3H), 3.86(1H), 4.25(1H), 4.65(1H), 8.11 (1H), 8.20-8.44(3H), 12.65(1H) |
| F-27 | H—L—Glu—OH | D | L—Pro—OH | H | $C_{15}H_{25}N_3O_6S \cdot HCl$ 137-142° C. decomp. | 8 | *1.33(3H), 1.38(3H), 1.76-2.24(6H), 2.30-2.60(2H), 2.93(1H), 3.50(2H), 3.60-3.95(3H), 4.21-4.30(1H), 4.92 (1H), 8.22-8.62(3H), 12.50(1H) |
| F-28 | H—L—Glu—OH | L | CH₂COOH \| L—Tyr—OH | H | $C_{21}H_{29}N_3O_9S \cdot HCl$ 120-124° C. decomp. | *8 | **1.26(6H), 2.01-2.19(2H), 2.34-2.62(2H), 2.80-2.96(1H), 3.12-3.25 (1H), 3.97(1H), 4.32(1H), 4.66(3H), 6.85(2H), 7.15(2H) |
| F-29 | H—L—Glu—OH | L | SO₃H \| DL—Phe—OH | H | $C_{19}H_{27}N_3O_9S_2 \cdot HCl$ 216-220° C. decomp. | 8 | *1.32(6H), 1.86-2.03(2H), 2.24-2.40 (2H), 2.63(1H), 3.05-3.22(2H), 3.78 (4H), 3.96(1H), 4.46-4.61(2H), 7.15-7.28(2H), 7.42-7.61(2H), 7.86(1H), 8.26-8.58(3H) |
| F-30 | H—L—Asp—OH | L | Gly—OH | H | $C_{13}H_{19}N_3O_6S \cdot HCl$ 146-149° C. decomp. | 8 | **1.39(3H), 1.45(3H), 2.94-3.21 (2H), 3.98(2H), 4.26(1H), 4.45(1H) |
| F-31 | H—L—Glu—OH | L | OH | H | $C_{10}H_{18}N_2O_5S \cdot HCl$ 52-55° C. decomp. | 8 | **1.38(3H), 1.44(3H), 2.10-2.24 (2H), 2.53-2.62(2H), 4.01(1H), 4.43 (1H) |
| F-32 | H | L | Gly—OH | H | $C_7H_{14}N_2O_3S \cdot HCl$ 57.5-59° C. decomp. | 8 | **1.46(3H), 1.54(3H), 4.01(3H) |

Compounds F-1 to F-3 and F-32 were isolated as respective hydrochlorides
*measured in DMSO-d₆
**measured in D₂O Working Example 1 (Synthesis of the Compound 8)

To the solution of (N-γ-L-glutamyl-D-penicillamyl)glycine hydrochloride (F-5) (0.3 g) in 1N-hydrochloric acid (0.81 ml) and methanol (1.6 ml), was added dropwise at room temperature the solution of sodium nitrite (0.11 g) in water (0.5 ml). After stirring at room temperature for 30 minutes, methanol was evaporated off under reduced pressure, and the solid precipitated by addition of acetone to the residue was washed with acetone, to give (N-γ-L-glutamyl-S-nitroso-D-penicillamyl)glycine (0.19 g).

Working Example 2 (Synthesis of the Compound 7)

To the solution of (N-γ-L-glutamyl-D-penicillamyl)glycine hydrochloride (0.5 g) in methanol (5 ml), was added at 0° C. the solution of ethyl nitrite in ethanol (10%) (1.1 ml). At the same temperature a drop of 4N-hydrochloric acid-methanol solution was added, and the mixture was stirred for 30 minutes. The solvent was evaporated off under reduced pressure, and the resultant crystals were washed with diethyl ether, to give (N-γ-L-glutamyl-S-nitroso-L-penicillamyl)glycine hydrochloride (0.5 g).

In the same way, the Compounds 1 to 6, 9 to 11, and 13 to 22 listed in Table 2 shown below were synthesized.

Working Example 3 (Synthesis of the Compound 12)

To the solution of (N-β-L-aspartyl-D-penicillamyl)glycine hydrochloride (0.2 g) in 1N-hydrochloric acid (0.56 ml) and water (1.0 ml), was added dropwise at room temperature the solution of sodium nitrite (0.077 g) in water (0.5 ml). The reaction mixture was stirred at room temperature for 30 minutes, loaded onto an LH-20 column, and eluted with water. The fractions containing the desired product were freeze-dried, to give (N-β-L-asparagyl-S-nitroso-D-penicillamyl)glycine (0.2 g).

Table 2 shows the structure, physical properties, and NMR data of the Compounds 1 to 34 obtained in the Working Examples.

TABLE 2

$$\underset{X-Pen-Y}{\overset{NO}{|}}$$

| Compound | X | Configuration of Pen | Y | Molecular formula Physical properties | Ex. No. | Related NMR spectra (δ, ppm) in D₂O | IR (KBr)(cm⁻¹) others |
|---|---|---|---|---|---|---|---|
| 1 | H | D | Gly—OH | C₇H₁₃N₃O₄S.HCl 44-48° C. decomp. | 2 | 1.93(3H), 2.11(3H), 4.02 (2H), 4.81(1H) | 3800-2350, 1735, 1681, 1550-1510, 1400, 1380, 1320, 1215, 1130, 1040, 1015, 660 |
| 2 | H—L—Glu—OH | D | OH | C₁₀H₁₇N₃O₆S.HCl amorphous | 2 | 1.91(3H), 1.94(3H), 1.96-2.24(2H), 2.34-2.61 (2H), 3.92(1H), 5.19(1H) | 3700-2200, 1733, 1655, 1515, 1395, 1375, 1220, 1126, 990, 663 |
| 3 | H—D—Glu—OH | D | OH | C₁₀H₁₇N₃O₆S.HCl 68-75° C. decomp. | 2 | 1.91(3H), 1.94(3H), 2.02-2.16(2H), 2.40-2.53 (2H), 3.94(1H), 5.17(1H) | 3800-2200, 1735, 1650, 1515, 1395, 1375, 1220, 1128, 990, 665 |
| 4 | Ac | L | Gly—OH | C₉H₁₅N₃O₅S amorphous | 2 | 1.89(3H), 1.92(3H), 1.97 (3H), 3.87-3.98(2H), 5.16(1H) | 3700-2250, 1740, 1655, 1520, 1375, 1215, 1135, 1035, 665 |
| 5 | H—L—Glu—OH | L | Gly—OH | C₁₂H₂₀N₄O₇S.HCl 84-89° C. decomp. | 2 | 1.88(3H), 1.98(3H), 1.90-2.22(2H), 2.30-2.67 (2H), 3.81-3.99(3H), 5.21(1H) | 3800-2150, 1738, 1650, 1525, 1415, 1392, 1371, 1215, 1130, 1035, 665 |
| 6 | H—L—Glu—OH | D | Gly—OH | C₁₂H₂₀N₄O₇S amorphous | 1 | 1.90(3H), 1.99(3H), 1.90-2.13(2H), 2.26-2.65 (2H), 3.67(1H), 3.77(2H) 5.21(1H) | 3700-2400, 1640, 1520, 1392, 1232 UV(H₂O):λmax = 340.0 nm |
| 7 | H—L—Glu—OH | D | Gly—OH | C₁₂H₂₀N₄O₇S.HCl 108-113° C. decomp. | 2 | 1.89(3H), 1.98(3H), 1.90-2.16(2H), 2.40-2.56 (2H), 3.91(1H), 3.93(2H) 5.20(1H) | 3800-2200, 1738, 1650, 1525, 1415, 1395, 1371, 1220, 1132, 1034, 665 |
| 8 | H—D—Glu—OH | D | Gly—OH | C₁₂H₂₀N₄O₇S.HCl 100-105° C. decomp. | 2 | 1.90(3H), 1.99(3H), 1.90-2.17(2H), 2.36-2.60 (2H), 3.91(1H), 3.94(2H) 5.21(1H) | 3800-2200, 1650, 1520, 1395, 1313, 1235, 1130, 665 |
| 9 | H—L—Glu— | L | Gly—OH | C₁₂H₂₀N₄O₇S.HCl 98-105° C. decomp. | 2 | 1.91(3H), 2.01(3H), 2.00-2.24(2H), 2.30-2.60 (2H), 3.95(2H), 4.09(1H) 5.27(1H) | 3700-2300, 1720, 1660, 1540, 1500, 1410, 1210, 665 |
| 10 | H—L—Asp—OH | D | Gly—OH | C₁₁H₁₈N₃O₆S amorphous | 3 | 1.93(3H), 2.01(3H), 2.69-3.06(2H), 3.92-4.02 (3H), 5.24(1H) | 3700-2300, 1738, 1658, 1526, 1385, 1218 UV(H₂O):λmax = 336.8 nm |
| 11 | H—L—Asp—OH | D | Gly—OH | C₁₁H₁₈N₃O₆S.HCl 95-100° C. decomp. | 2 | 1.87(3H), 1.96(3H), 2.80-3.09(2H), 3.80-4.04 (2H), 4.27(1H), 5.18(1H) | 3700-2200, 1736, 1653, 1535, 1210, 665 |
| 12 | H—L—Glu—OH | L | L—Ala—OH | C₁₃H₂₂N₄O₇S.HCl 107-112° C. decomp. | 2 | 1.37(3H), 1.91(3H), 2.01 (3H), 1.90-2.17(2H), 2.39-2.55(2H), 3.92(1H) 4.23-4.38(1H), 5.18(1H) | 3700-2200, 1730, 1650, 1520, 1455, 1390, 1370, 1218, 1150, 835, 665 |
| 13 | H—L—Glu—OH | L | L—Val—OH | C₁₅H₂₆N₄O₇S.HCl 118-122° C. decomp. | 2 | 0.86(3H), 0.89(3H), 1.89 (3H), 1.98(3H), 0.80-2.23(3H), 2.37-2.58(2H) 3.91(1H), 4.12-4.23(1H) 5.25(1H) | 3700-2250, 1725, 1650, 1520, 1394, 1372, 1220, 1145, 1128, 665 |
| 14 | H—L—Glu—OH | D | L—Val—OH | C₁₅H₂₆N₄O₇S.HCl 112-117° C. decomp. | 2 | 0.87(3H), 0.91(3H), 1.90 (3H), 1.96(3H), 1.95-2.23(3H), 2.34-2.54 (2H), 3.90(1H), 4.07-4.26(1H), 5.30(1H) | 3700-2250, 1738, 1650, 1522, 1392, 1370, 1220, 1145, 668 |
| 15 | H—L—Glu—OH | L | L—Leu—OH | C₁₆H₂₈N₄O₇S.HCl 120-124° C. decomp. | 2 | 0.70-0.92(6H), 1.46-1.73(3H), 1.79-2.19 (2H), 1.89(3H), 1.97(3H), 2.35-2.60(2H), 3.89(1H) 4.25-4.40(1H), 5.17(1H) | 3700-2200, 1725, 1645, 1520, 1390, 1370, 1225, 1210, 1150, 665 |

TABLE 2-continued $$X-Pen-Y \atop | \atop NO$$

| Compound | X | Configuration of Pen | Y | Molecular formula Physical properties | Ex. No | Related NMR spectra (δ, ppm) in $D_2O$ | IR (KBr)(cm$^{-1}$) others |
|---|---|---|---|---|---|---|---|
| 16 | H—L—Glu—OH | L | L—Pro—OH | $C_{15}H_{24}N_4O_7S \cdot HCl$ 120–125° C. decomp. | 2 | 1.87(3H), 2.02(3H), 1.64–2.52(8H), 3.68–3.93 (3H), 3.86(1H), 5.56(1H) | 3650–2200, 1740, 1625, 1505, 1450, 1210, 1190, 665 |
| 17 | H—L—Glu—OH | L | L—Phe—OH | $C_{19}H_{26}N_4O_7S \cdot HCl$ 122–127° C. decomp. | 2 | 1.74(3H), 1.87(3H), 1.90–2.19(2H), 2.21–2.50 (2H), 2.75–2.98(1H), 3.08–3.28(1H), 3.89(1H) 4.55–4.70(1H), 5.10(1H) 7.06–7.40(5H) | 3800–2200, 1730, 1650, 1520, 1459, 1395, 1374, 1225, 1132, 703 |
| 18 | H—L—Glu—OH | L | L—Tyr—OH | $C_{19}H_{26}N_4O_8S \cdot HCl$ 107–112° C. decomp. | 2 | 1.76(3H), 1.86(3H), 1.94–2.14(2H), 2.20–2.46 (2H), 2.77(1H), 3.15(1H) 3.87(1H), 4.55–4.70(1H) 5.08(1H), 6.70(2H), 7.03(1H) | 3800–2200, 1730, 1650, 1518, 1450, 1395, 1375, 1230, 1130, 1110, 835, 670 |
| 19 | H—L—Glu—OH | L | L—Glu—OH | $C_{15}H_{24}N_4O_9S \cdot HCl$ 80–85° C. decomp. | 2 | 1.88(3H), 1.97(3H), 1.70–2.50(8H), 3.90(1H), 4.39(1H), 5.17(1H) | 3800–2230, 1730, 1655, 1520, 1455, 1395, 1375, 1220, 1135, 665 |
| 20 | H—L—Glu—OH | L | NHCHPh$_2$ | $C_{23}H_{28}N_4O_5S \cdot HCl$ 120–130° C. decomp. | 2 | *1.91(3H), 1.96(3H), 2.20–2.57(4H), 3.40(1H), 3.82(1H), 5.46(1H), 6.18 (1H), 7.18–7.40(10H), 8.40(3H), 8.62(1H), 9.51 (1H) | 3700–2150, 1740, 1650, 1520, 1458, 1393, 1372, 1232, 1125, 1032, 702 |
| 21 | H—L—Glu—OH | L | L—Asp—OH | $C_{14}H_{21}N_4O_9S \cdot HCl$ 84–88° C. decomp. | 2 | 1.92(3H), 2.00(3H), 2.02–2.19(2H), 2.42–2.55 (2H), 2.86–2.96(2H), 3.93(1H), 4.72(1H), 5.20 (1H) | 3700–2200, 1735, 1650, 1525, 1225, 670 |
| 22 | H—L—Glu—OH | L | L—Met—OH | $C_{15}H_{25}N_4O_7S \cdot HCl$ 104–109° C. decomp. | 2 | 1.82–2.26(4H), 1.92(3H), 2.01(3H), 2.03(3H), 2.37–2.66(4H), 3.95(1H), 4.54(1H), 5.20(1H) | 3700–2200, 1735, 1650, 1520, 1225, 670 |
| 23 | H—L—Glu—OH | L | L—Ile—OH | $C_{16}H_{28}N_4O_7S \cdot HCl$ 109–115° C. decomp. | 2 | 0.82(3H), 0.88(3H), 1.22 (1H), 1.27–1.53(1H), 1.77–2.24(3H), 1.91(3H), 1.99(3H), 2.41–2.53 (2H), 3.94(1H), 4.24 (1H), 5.25(1H) | 3700–2200, 1730, 1650, 1520, 1220, 670 |
| 24 | H—L—Glu—OH | D | NHCHPh$_2$ | $C_{23}H_{28}N_4O_5S \cdot HCl$ 150–155° C. decomp. | 2 | *1.80–2.20(2H), 1.91 (3H), 1.96(3H), 2.26–2.44(2H), 3.60(1H), 3.81 (1H), 5.45(1H), 6.17(1H), 7.20–7.43(10H), 8.32 (3H), 8.56(1H), 9.49(1H) | 3700–2200, 1735, 1645, 1520, 1230, 700 |
| 25 | H—L—Glu—OH | D | L—Leu—OH | $C_{16}H_{28}N_4O_7S \cdot HCl$ 130–136° C. decomp. | 2 | 0.75–1.01(6H), 1.45–1.76(3H), 1.92(3H), 1.96 (3H), 2.06–2.20(2H), 2.43–2.61(2H), 3.95(1H), 4.30(1H), 5.27(1H) | 3700–2200, 1730, 1645, 1520, 1390, 1370, 1225, 665 |
| 26 | H—L—Glu—OH | D | L—Phe—OH | $C_{19}H_{25}N_4O_7S \cdot HCl$ 120–125° C. decomp. | 2 | 1.63(6H), 1.89–2.25 (2H), 2.30–2.66(2H), 2.94(1H), 3.18–3.43 (1H), 3.91(1H), 4.63–4.70(1H), 5.12(1H), 7.05–7.50(5H) | 3700–2200, 1730, 1650, 1520, 1455, 1390, 1370, 1220, 1125, 700, 665 |
| 27 | H—L—Glu—OH | D | L—Glu—OH | $C_{15}H_{24}N_4O_9S \cdot HCl$ 91–96° C. decomp. | 2 | 0.80–2.27(4H), 1.92 (3H), 1.97(3H), 2.34–2.64(4H), 3.95(1H), 4.34(1H), 5.25(1H) | 3700–2200, 1730, 1650, 1520, 1220, 665 |

TABLE 2-continued $$X-\underset{\underset{NO}{|}}{Pen}-Y$$

| Com- pound | X | Config- uration of Pen | Y | Molecular formula Physical properties | Ex. No | Re- lated NMR spectra (δ, ppm) in $D_2O$ | IR (KBr)(cm$^{-1}$) others |
|---|---|---|---|---|---|---|---|
| 28 | H—L—Glu—OH ⌐ | L | L—Ser—OH | $C_{13}H_{23}N_4O_8S \cdot HCl$ 89-92° C. decomp. | 2 | 1.94(3H), 2.03(3H), 2.05-2.22(2H), 2.42-2.55(2H), 3.79-4.02 (3H), 4.52(1H), 5.29(1H) | 3800-2200, 1735, 1650, 1520, 1390, 1370, 1225, 1135, 1070, 665 |
| 29 | H—L—Glu—OH ⌐ | D | L—Pro—OH | $C_{15}H_{24}N_4O_7S \cdot HCl$ 77-81° C. decomp. | 2 | 1.87(3H), 1.90-2.36 (6H), 2.01(3H), 2.43-2.57(2H), 3.68-3.89 (2H), 3.96(1H), 4.32 (1H), 5.64(1H) | 3700-2200, 1735, 1630, 1510, 1450, 1220, 1190, 665 |
| 30 | H—L—Glu—OH ⌐ | L | CH$_2$COOH \| L—Tyr—OH | $C_{21}H_{28}N_4O_{10}S \cdot HCl$ 108-112° C. decomp. | 2 | 1.77(3H), 1.87(3H), 1.96-2.12(2H), 2.31-2.43 (2H), 2.76-2.92(1H), 3.10-3.26(1H), 3.90 (1H), 4.51-4.70(1H), 4.64(2H), 5.11(1H), 6.82 (2H), 7.13(2H) | 3700-2200, 1735, 1650, 1515, 1220, 835, 670 |
| 31 | H—L—Glu—OH ⌐ | L | SO$_3$H \| DL—Phe—OH | $C_{19}H_{26}N_4O_{10}S_2 \cdot HCl$ 140-145° C. decomp. | 2 | 1.79(3H), 1.89(3H), 1.95-2.21(2H), 2.31-2.43 (2H), 2.82-2.97(1H), 3.06-3.19(1H), 3.93 (1H), 4.52-4.73(1H), 5.13(1H), 7.28-7.43 (2H), 7.59-7.78(2H) | 3700-2200, 1735, 1655, 1520, 1215, 1180, 1120, 1035, 1005, 680 |
| 32 | H—L—Asp—OH ⌐ | L | Gly—OH | $C_{11}H_{18}N_4O_7S \cdot HCl$ 85-90° C. decomp. | 2 | 1.91(3H), 2.00(3H), 2.87-3.14(2H), 3.97(2H), 4.24(1H), 5.24(1H) | 3750-2200, 1740, 1655, 1535, 1410, 1390, 1210, 1130, 660 |
| 33 | H—L—Glu—OH ⌐ | L | OH | $C_{10}H_{17}N_3O_6S \cdot HCl$ 73-80° C. decomp. | 2 | 1.93(3H), 1.96(3H), 2.06-2.18(2H), 2.44-2.55 (2H), 3.98(1H), 5.19(1H) | 3800-2200, 1735, 1650, 1520, 1210, 1115, 660 |
| 34 | H | L | Gly—OH | $C_7H_{13}N_3O_4S \cdot HCl$ 63-68° C. decomp | 2 | 1.95(3H), 2.12(3H), 4.05 (2H), 4.83(1H) | 3800-2200, 1735, 1680, 1540, 1505, 1400, 1315, 1200, 655 |

Compounds 1-3, 5, 7-9, and 11-34 were isolated as respective hydrochlorides
*measured by using DMSO-d$_6$ as the solvent and TMS as the internal standard

PREPARATION EXAMPLES

Preparation Example 1

| (1) Compound 1 | 2 g |
|---|---|
| (2) lactose | 196 g |
| (3) corn starch | 50 g |
| (4) magnesium stearate | 2 g |

(1), (2) and 20 g of corn starch were mixed and granulated together with a paste made from 15 g of corn starch, to which 15 g of cornstarch and (4) were added. The mixture was compressed with a compress-tableting machine, to produce 2000 tablets of 3 mm in diameter containing 1 mg of (1) in each tablet.

PREPARATION EXAMPLE 2

| (1) Compound 2 | 4 g |
|---|---|
| (2) lactose | 194 g |
| (3) corn starch | 40 g |
| (4) magnesium stearate | 2 g |

(1), (2) and 15 g of corn starch were mixed and granulated together with a paste made from 15 g of corn starch, to which 10 g of corn starch and (4) were added. The mixture was compressed with a compress-tableting machine, to produce 2000 tablets of 5 mm in diameter containing 2 mg of (1) in each tablet.

PREPARATION EXAMPLE 3

| (1) Compound 1 | 100 mg |
|---|---|
| (2) Avicel (crystalline cellulose) | 300 mg |
| (3) lactose | 595 mg |
| (4) magnesium stearate | 5 mg |

(1), (2), (3) and (4) described above were mixed thoroughly, and compressed directly with a compress-tableting machine, to produce 100 sublingual tablets (3 mm in diameter) containing 1 mg of (1) in each tablet.

EXPERIMENTAL EXAMPLE 1

In a 20 ml-tank (37° C., aerated with 95% $O_2$+5% $CO_2$, pH 7.4), a specimen (pig left coronary descending artery (LAD), or rat aorta) was suspended. The specimen was allowed to contract by addition of $PGF_{2\alpha}$(6 μM) for pig coronary artery or KCl (60 mM) or TEA (45 mM)+Ba (0.3 mM) for rat aorta, and then a test compound was added at a time or cumulatively; the relaxing effect of the compound on the constrictive tension was examined: the Compounds 1 and 2 showed a powerful relaxing effect.

Experiment Example 2

Relaxing effects on KCl induced contraction in isolated rat aorta

Ring preparations of rat thoracic aorta were placed in 20 ml organ baths containing Krebs-Hemseleit solution kept at 37° C., a pH of 7.4 and gassed with 95% $CO_2 - 5\% O_2$. After steady state contraction induced by 60 mM KCl, vasorelaxing effects of test compounds ($10^{-6}$, $10^{-7}$ mol/l) were examined. The vasorelaxing effects were expressed as % relaxation from the maximum contraction induced by 60 mM KCl. The relaxing effects are shown in Table 3.

TABLE 3

| Compound | Retension $10^{-7}$ M | time/min | Retension $10^{-6}$ M | time/min |
|---|---|---|---|---|
| 2 | 18 | 24 | 62 | >30 |
| 3 | 19 | 17 | 50 | >30 |
| 5 | 16 | 25 | 47 | >30 |
| 7 | 11 | >30 | 64 | >30 |
| 11 | 12 | 20 | 37 | >30 |
| 13 | 19 | >30 | 85 | >30 |
| 14 | 11 | 12 | 74 | >30 |
| 17 | 20 | 17 | 66 | >30 |
| 19 | 19 | 20 | 58 | >30 |
| 24 | 26 | >30 | 75 | >30 |

What is claimed is:
1. A compound of the formula:

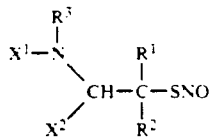

wherein $R^1$ and $R^2$ are independently a hydrogen atom or an unsubstituted or substituted hydrocarbon group, or $R^1$ and $R^2$ taken together form a ring of the formula —$(CH_2)_n$— wherein n is an integer of 2 to 6; $R^3$ is a hydrogen atom, an acyl group or an unsubstituted or substituted hydrocarbon group; $X^1$ is a hydrogen atom, an acyl group, a lower alkoxy group or an unsubstituted or substituted hydrocarbon group; $X^2$ is an acyl group, a carboxyl group, a carboxyl group which is esterified or a carboxyl group forming an amide;

wherein said substituted hydrocarbon groups are substituted with 1 to 3 substituents selected from the groups consisting of halogen, nitro, nitrile, hydroxyl, carboxyl, $C_{1-4}$-alkoxy, $C_{1-4}$-alkylthio, amino, mono- or di-$_{1-4}$-alkyl substituted amino, mono- or di-aralkyl substituted amino, mono- or di-pyridylcarbonyl substituted amino, $C_{1-4}$-alkoxycarbonyl, hydroxycarbonyl, $C_{1-6}$-alkylcabonyl, cyclo-$C_{3-6}$-alkylcarbonyl, carbamoyl, mono- or di-$C_{1-4}$-alkyl substituted carbamoyl, and phenyl, phenoxy, benzoyl, phenoxycarbonyl, phenyl-$C_{1-4}$- alkylcarbamoyl and phenylcarbamoyl wherein the phenyl ring is unsubstituted or substituted with 1 to 4 substituents selected from the group consisting of $C_{1-4}$-alkyl, halogen, hydroxyl, benzyloxy, amino, mono- or di-$C_{1-4}$-alkyl substituted amino, nitro and $C_{1-4}$-alkoxycarbonyl, provided that when $X^2$ is a carboxyl group, $X^1$ is not a hydrogen atom or acetyl group and that when both $R^1$ and $R^2$ are hydrogen atoms $X^1$ is not acetyl group or γ-glutamyl group, or a pharmaceutically acceptable salt thereof.

2. A compound according to claim 1, wherein $R^1$ and $R^2$ are independently an unsubstituted or substituted hydrocarbon group, or $R^1$ and $R^2$ taken together form a ring of the formula —$(CH_2)_n$— wherein n is an integer of 2 to 6.

3. A compound according to claim 1, wherein $X^1$ is an amino acid derived acyl.

4. A compound according to claim 1, wherein $R^1$ and $R^2$ are independently an unsubstituted or substituted hydrocarbon group; $R^3$ is a hydrogen atom, an acyl group or an unsubstituted or substituted hydrocarbon group; $X^1$ is an amino acid derived acyl; and $X^2$ is an acyl group, a carboxyl group, a carboxyl group which is esterified or a carboxyl group forming an amide.

5. A compound according to claim 1, wherein the unsubstituted or substituted hydrocarbon group represented by $R^1$, $R^2$, $R^3$ or $X^1$ is an unsubstituted or substituted $C_{1-4}$ chain saturated hydrocarbon group, an unsubstituted or substituted $C_{2-4}$ chain unsaturated hydrocarbon group, an unsubstituted or substituted $C_{3-14}$ cyclic saturated hydrocarbon group or an unsubstituted or substituted $C_{6-10}$ cyclic unsaturated hydrocarbon group, wherein each of said substituted hydrocarbon groups are substituted with one to three substituents selected from the group consisting of halogen atom, nitro, nitrile, hydroxyl, carboxyl, $C_{1-4}$ alkoxy, $C_{1-4}$ alkylthio, amino, mono- or di-$C_{1-4}$-alkyl amino, mono- or di-aralkylamino, mono- or di-pyridylcarbonylamino, $C_{1-6}$-alkylcarbonyl, $C_{1-4}$ alkoxycarbonyl, cyclo $C_{3-6}$-alkylcarbonyl, carbamoyl, mono- or di-$C_{1-4}$ alkylcarbamoyl, and phenyl, phenoxy, benzoyl, phenoxycarbonyl, phenyl $C_{1-4}$ alkylcarbamoyl or phenylcarbamoyl group, in which each of said phenyl groups is unsubstituted or substituted by 1 to 4 substituents selected from the group consisting of $C_{1-4}$ alkyl, halogen atom, hydroxyl, benzyloxy, amino, mono- or di-$C_{1-4}$ alkylamino, nitro and $C_{1-4}$ alkoxycarbonyl.

6. A compound according to claim 1, wherein the acyl group represented by $R^3$, $X^1$ or $X^2$ is a carboxylic, carbamic, sulfonic or oxycarboxylic acyl group, each of which is unsubstituted or substituted by one to three substituents selected from the group consisting of halogen atom, nitro, nitrile, hydroxyl, carboxyl, $C_{1-4}$ alkoxy, $C_{1-4}$ alkylthio, amino, mono- or di-$C_{1-4}$ alkylamino, mono- or di-aralkylamino, mono- or di-pyridylcarbonylamino, $C_{1-6}$ alkylcarbonyl, $C_{1-4}$ alkoxycarbonyl, cyclo $C_{3-6}$ alkylcarbonyl, carbamoyl, mono- or di-$C_{1-4}$ alkylcarbamoyl, and phenyl, phenoxy, benzoyl, phenoxycarbonyl, phenyl $C_{1-4}$ alkylcarbamoyl or phenylcarbamoyl group, in which each of said phenyl groups is unsubstituted or substituted by 1 to 4 substituents selected from the group consisting of $C_{1-4}$ alkyl, halogen atom, hydroxyl, benzyloxy, amino, mono- or di-$C_{1-4}$ alkylamino, nitro and $C_{1-4}$ alkoxycarbonyl.

7. A compound according to claim 1, wherein the lower alkoxy group is a $C_{1-6}$ alkoxy group.

8. A compound according to claim 1, wherein the carboxyl group which is esterified is a group of the formula: —CO—OR$^5$ wherein R$^5$ is an unsubstituted or substituted hydrocarbon group as defined in claim 1.

9. A compound according to claim 1, wherein the carboxyl group forming an amide is a group of the formula:

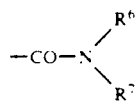

wherein $R^6$ is a hydrogen atom, an unsubstituted hydrogen group or a substituted hydrocarbon group as defined in claim 1, and $R^7$ is a hydrogen atom or a lower alkyl group, or $R^6$ and $R^7$ form a cyclic amino group together with the adjacent nitrogen atom.

10. A compound according to claim 1, wherein $R^1$ and $R^2$ are independently a chain saturated or cyclic unsaturated hydrocarbon group or $R^1$ and $R^2$ together with the adjacent carbon atom form cyclopentyl or cyclohexyl.

11. A compound according to claim 1, wherein $R^1$ and $R^2$ are independently a $C_{1-6}$ alkyl group.

12. A compound according to claim 1, wherein $R^1$ and $R^2$ are methyl.

13. A compound according to claim 1, wherein $R^3$ is a hydrogen atom or an acyl group.

14. A compound according to claim 13, wherein the acyl group is $C_{1-6}$ alkyl carbonyl or $C_{6-10}$ aryl carbonyl.

15. A compound according to claim 1, wherein $R^3$ is a hydrogen atom.

16. A compound according to claim 1, wherein $X^1$ is a hydrogen atom or an acyl group.

17. A compound according to claim 16, wherein the acyl group is an amino acid derived acyl group.

18. A compound according to claim 17, wherein the amino acid is glycine, alanine, glutamic acid, leucine, isoleucine, phenylalanine, aspartic acid, cysteine, sarcosine, glutamine, asparagine or proline.

19. A compound according to claim 17, wherein the amino acid is glycine, aspartic acid, asparagine, glutamic acid, glutamine or phenylalanine.

20. A compound according to claim 17, wherein the amino acid is glutamic acid or aspartic acid.

21. A compound according to claim 1, wherein $X^2$ is a carboxyl group or a carboxyl group which is esterified.

22. A compound according to claim 1, wherein $X^2$ is a carboxyl or carbamic acyl group.

23. A compound according to claim 22, wherein the carbamic acyl group is carbonyl amino or a carboxyl group forming an amide with an amino acid.

24. A compound according to claim 23, wherein the amino acid is glycine, alanine, glutamic acid, leucine, isoleucine, phenylalanine, aspartic acid, cysteine, sarcosine, glutamine, asparagine or proline.

25. A compound according to claim 23, wherein the amino acid is glycine, aspartic acid, asparagine, phenylalanine, glutamic acid or glutamine.

26. A compound according to claim 1, wherein $R^1$ and $R^2$ are independently $C_{1-6}$ alkyl, phenyl or naphthyl, or $R^1$ and $R^2$ form cyclopentyl or cyclohexyl together with the adjacent carbon atom; $R^3$ is a hydrogen atom or a $C_{6-10}$ aromatic acyl group; $X^1$ is a hydrogen atom or an amino acid derived acyl group in which said amino acid is selected from the group consisting of glycine, aspartic acid, phenylalanine, asparagine, glutamic acid and glutamine; $X^2$ is a carboxyl group, carbonylamino or a carboxyl group forming an amide with an amino acid in which said amino acid is selected from the group consisting of glycine, aspartic acid, phenylalanine, asparagine, glutamic acid and glutamine.

27. The compound N-(N-L-γ-Glutamyl-D-penicillamyl)glycine.

28. The compound N-(N-L-γ-Glutamyl-L-Penicillamyl)-L-valine.

29. The compound N-(N-L-γ-Glutamyl-L-penicillamyl)-L-phenylalanine.

30. The compound N-(N-L-γ-Glutamyl-L-penicillamyl)-L-glutamic acid.

31. The compound N-(N-L-γ-Glutamyl-D-penicillamyl-diphenylmethylamine.

32. A pharmaceutical composition for combatting hypertension or angina pectoris which comprises (a) as the active ingredient, an effective amount of a compound according to claim 1 or a pharmaceutically acceptable salt thereof and (b) a pharmaceutically acceptable carrier, excipient or diluent therefor.

33. A method for combatting hypertension or angina pectoris in a mammal in need thereof, which comprises administering to said mammal an effective amount of a compound according to claim 1 or a pharmaceutically acceptable salt thereof.

* * * * *